US006222019B1

(12) United States Patent
Ni et al.

(10) Patent No.: US 6,222,019 B1
(45) Date of Patent: Apr. 24, 2001

(54) HUMAN IRAK-2 ANTIBODIES

(75) Inventors: Jian Ni, Rockville; Ping Feng, Gaithersburg, both of MD (US); Marta Muzio, Milan (IT); Vishva M. Dixit, Los Altos Hills, CA (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/307,185

(22) Filed: May 7, 1999

Related U.S. Application Data

(62) Division of application No. 08/980,060, filed on Nov. 26, 1997, now Pat. No. 5,965,421.

(51) Int. Cl.[7] .................................................. C07K 16/00
(52) U.S. Cl. ..................................... 530/387.1; 530/388.1
(58) Field of Search ...................... 530/388.1; 424/130.1; 435/70.21

(56) References Cited

FOREIGN PATENT DOCUMENTS

WO 94/17187    8/1994 (WO).
WO 97/00690    1/1997 (WO).

OTHER PUBLICATIONS

Bergers, G. et al., "Alternative promoter usage of the Fos–responsive gene Fit–1 generates mRNA isoforms coding for either secreted or membrane–bound proteins related to the IL–1 receptor," *EMBO J.* 13(5):1176–1188 (1994).
Bird, T.A. et al., "Evidence that MAP (Mitogen–Activated Protein) Kinase Activation May Be a Necessary but Not Sufficient Signal for a Restricted Subset of Responses in IL–1–Treated Epidermoid Cells," *Cytokine* 4(6):429–440 (1992).
Bonnert, T.P. et al., "The cloning and characterization of human MyD88: a member of an IL–1 receptor related family," *FEBS Lett.* 402(1):81–84 (Jan. 1997).
Cao, Z. et al., "IRAK: A Kinase Associated with the Interleukin–1 Receptor," *Science* 271:1128–1131 (Feb. 1996).
Cao, Z. et al., "TRAF6 is a signal transducer for interleukin–1," *Nature* 383:443–446 (Oct. 1996).
Cleary, M.L. et al., "Cloning and Structural Analysis of cDNAs for bcl–2 and a Hybrid bcl–2/Immunoglobulin Transcript Resulting from the t(14;18) Translocation," *Cell* 47:19–28 (1986).
Fleischmann, R.D. et al., "Whole–Genome Random Sequencing and Assembly of *Haemophilus influenzae* Rd," *Science* 269:496–512 (1995).
Galindo, R.L. et al., "Interaction of the pelle kinase with the membrane–associated protein tube is required for transduction of the dorsoventral signal in Drosophila embryos," *Development* 121(7):2209–2218 (1995).
Gay, N.J. and F.J. Keith, "Drosophila Toll and IL–1 receptor," *Nature* 351:355–356 (1991).
Gayle, M.A. et al., "Cloning of a Putative Ligand for the T1/ST2 Receptor," *J. Biol. Chem.* 271(10):5784–5789 (Mar. 1996).
Greenfeder, S.A. et al., "Molecular Cloning and Characterization of a Second Subunit of the Interleukin 1 Receptor Complex," *J. Biol. Chem.* 270(23):13757–13765 (1995).
Großhans, J. et al., "Activation of the kinase Pelle by Tube in the dorsoventral signal transduction pathway of Drosophila embryo," *Nature* 372:563–566 (1994).
Hardiman, G. et al., "Molecular characterization and modular analysis of human MyD88," *Oncogene* 13(11):2467–2475 (Dec. 1996).
Hashimoto, C. et al., "The Toll Gene of Drosophila, Required for Dorsal–Ventral Embryonic Polarity, Appears to Encode a Transmembrane Protein," *Cell* 52:269–279 (1988).
Hofmann, K. and J. Tschopp, "The death domain motif found in Fas (Apo–1) and TNF receptor is present in proteins involved in apoptosis and axonal guidance," *FEBS Lett.* 371(3):321–323 (1995).
Hopp, T.P., "Evidence from sequence information that the interleukin–1 is a transmembrane GTPase," *Protein Science* 4(9):1851–1859 (1995).
Hultmark, D., "Macrophage Differentiation Marker MyD88 Is a Member of the Toll/IL–1 Receptor Family," *Biochem. Biophys. Res. Commun.* 199(1):144–146 (1994).
Klemenz, R. et al., "Serum– and oncoprotein–mediated induction of a gene with sequence similarity to the gene encoding carcinoembryonic antigen," *Proc. Natl. Acad. Sci. USA* 86(15):5708–5712 (1989).
Kumar, S. et al., "ST2/T1 Protein Functionally Binds to Two Secreted Proteins from Balb/c 3T3 and Human Umbilical Vein Endothelial Cells but Does Not Bind Interleukin 1," *J. Biol. Chem.* 270(46):27905–27913 (1995).
Letsou, A. et al., "Domain mapping of tube, a protein essential for dorsoventral patterning of the Drosophila embryo," *EMBO J.* 12(9):3449–3458 (1993).
Lord, K.A. et al., "Nucleotide sequence and expression of a cDNA encoding MyD88, a novel myeloid differentiation primary response gene induced by IL6," *Oncogene* 5(7):1095–1097 (1990).
Medzhitov, R. et al., "A human homologue of the Drosophila Toll protein signals activation of adaptive immunity," *Nature* 388:394–397 (Jul. 1997).

(List continued on next page.)

*Primary Examiner*—Susan Ungar
*Assistant Examiner*—Gary B Nickol
(74) *Attorney, Agent, or Firm*—Sterne, Kessler, Goldstein & Fox

(57) ABSTRACT

The present invention relates to a novel IRAK-2 protein which is a member of the IL-1 signaling pathway. In particular, isolated nucleic acid molecules are provided encoding the human IRAK-2 protein. IRAK-2 polypeptides are also provided as are vectors, host cells and recombinant methods for producing the same. Also provided are diagnostic methods for detecting IRAK-2 related disorders and therapeutic methods for treating IRAK-2 related disorders.

10 Claims, 17 Drawing Sheets

OTHER PUBLICATIONS

Mitcham, J.L. et al., "T1/ST2 Signaling Establishes It as a Member of an Expanding Interleukin–1 Receptor Family," *J. Biol. Chem.* 271(10):5777–5783 (Mar. 1996).

Muzio, M. et al., "IRAK (Pelle) family member IRAK–2 and MyD88 as proximal mediators of IL–1 signaling," *Science* 278:1612–1615 (1997).

Norris, J.L. and J.L. Manley, "Functional interactions between the pelle kinase, Toll receptor, and tube suggest a mechanism for activation of dorsal," *Genes Dev.* 10(7):862–872 (Apr. 1996).

Nomura, N. et al., "Prediction of the Coding Sequences of Unidentified Human Genes. I. The Coding Sequences of 40 New Genes (KIAA0001–KIAA0040) Deduced by Analysis of Randomly Sampled cDNA Clones from Human Immature Myeloid Cell Line KG–1," *DNA Res.* 1:27–35 (1994).

Ostrowski, J. et al., "A Serine/Threonine Kinase Activity Is Closely Associated with a 65–kDa Phosphoprotein Specifically Recognized by the κB Enhancer Element," *J. Biol. Chem.* 266(19):12722–12733 (1991).

Parnet, P. et al., "IL–1Rrp Is a Novel Receptor–like Molecule Similar to the Type I Interleukin–1 Receptor and Its Homologues T1/ST2 and IL–1R AcP," *J. Biol. Chem.* 271(8):3967–3970 (Feb. 1996).

Reikerstorfer, A. et al., "Low Affinity Binding of Interleukin–1β and Intracellular Signaling via NF–κB Identify Fit–1 as a Distant Member of the Interleukin–1 Receptor Family," *J. Biol. Chem.* 270(30):17645–17648 (1995).

Schneider, D.S. et al., "Dominant and recessive mutations define functional domains of Toll, a transmembrane protein required for dorsal–ventral polarity in the Drosophila embryo," *Genes Dev.* 5:797–807 (1991).

Sims, J.E. et al., "cDNA Expression Cloning of the IL–1 Receptor, a Member of the Immunoglobulin Superfamily," *Science* 241:585–589 (1988).

Sims, J.E. et al., "Genomic Organization of the Type I and Type II IL–1 Receptors," *Cytokine* 7(6):483–490 (1995).

Singh, R. et al., "Cytosolic Domain of the Type I Interleukin–1 Receptor Spontaneously Recruits Signaling Molecules to Activate a Proinflammatory Gene," *J. Clin. Invest.* 100(2):419–428 (Jul. 1997).

Tominaga, S., "A putative protein of a growth specific cDNA from BALB/c–3T3 cells is highly similar to the extracellular portion of mouse interleukin 1 receptor," *FEBS Lett.* 258(2):301–304 (1989).

Yanagisawa, K. et al., "Presence of a novel primary response gene ST2L, encoding a product highly similar to the interleukin 1 receptor type 1," *FEBS Lett.* 318(1):83–87 (1993).

NCBI Entrez Nucleotide Query, GenBank Accession No. C05986, from Takeda, J. (Oct. 1996).

NCBI Entrez Nucleotide Query, GenBank Accession No. W79504, from Hillier, L. et al. (Oct. 1996).

NCBI Entrez Nucleotide Query, GenBank Accession No. AA171941, from Hillier, L. et al. (Dec. 1996).

NCBI Entrez Nucleotide Query, GenBank Accession No. AA176605, from Hillier, L. et al. (Dec. 1996).

NCBI Entrez Nucleotide Query, GenBank Accession No. N52479, from Hillier, L. et al., (Jan. 1997).

NCBI Entrez Nucleotide Query, GenBank Accession No. AA368936, from Adams, M.D. et al. (Apr. 1997).

NCBI Entrez Nucleotide Query, GenBank Accession No. AA469327, from NCI–CGAP (Aug. 1997).

NCBI Entrez Nucleotide Query, GenBank Accession No. AA262752, from NCI–CGAP (Aug. 1997).

NCBI Entrez Nucleotide Query, GenBank Accession No. AA491814, from NCI–CGAP (Aug. 1997).

NCBI Entrez Nucleotide Query, GenBank Accession No. AA557911, from NCI–CGAP (Aug. 1997).

NCBI Entrez Nucleotide Query, GenBank Accession No. AA503258, from NCI–CGAP (Aug. 1997).

NCBI Entrez Nucleotide Query, GenBank Accession No. AA528390, from NCI–CGAP (Aug. 1997).

NCBI Entrez Nucleotide Query, GenBank Accession No. AA515224, from NCI–CGAP (Aug. 1997).

NCBI Entrez Nucleotide Query, GenBank Accession No. AA482768, from NCI–CGAP (Aug. 1997).

NCBI Entrez Nucleotide Query, GenBank Accession No. AA563770, from NCI–CGAP (Sep. 1997).

NCBI Entrez Nucleotide Query, GenBank Accession No. AA582554, from NCI–CGAP (Sep. 1997).

NCBI Entrez Nucleotide Query, GenBank Accession No. AA583955, from NCI–CGAP (Sep. 1997).

NCBI Entrez Nucleotide Query, GenBank Accession No. AA579566, from NCI–CGAP (Sep. 1997).

NCBI Entrez Nucleotide Query, GenBank Accession No. AA579179, from NCI–CGAP (Sep. 1997).

NCBI Entrez Nucleotide Query, GenBank Accession No. AA602557, from NCI–CGAP (Sep. 1997).

NCBI Entrez Nucleotide Query, GenBank Accession No. AA587604, from NCI–CGAP (Sep. 1997).

NCBI Entrez Nucleotide Query, GenBank Accession No. AA581903, from NCI–CGAP (Sep. 1997).

NCBI Entrez Nucleotide Query, GenBank Accession No. AA584489, from NCI–CGAP (Sep. 1997).

NCBI Entrez Nucleotide Query, GenBank Accession No. AA613624, from NCI–CGAP (Oct. 1997).

NCBI Entrez Nucleotide Query, GenBank Accession No. AA613627, from NCI–CGAP (Oct. 1997).

NCBI Entrez Nucleotide Query, GenBank Accession No. AA640053, from NCI–CGAP (Oct. 1997).

NCBI Entrez Nucleotide Query, GenBank Accession No. AA631497, from NCI–CGAP (Oct. 1997).

NCBI Entrez Nucleotide Query, GenBank Accession No. AA527209, from NCI–CGAP (Nov. 1997).

NCBI Entrez Nucleotide Query, GenBank Accession No. AA669840, from Jia, L. et al. (Nov. 1997).

NCBI Entrez Nucleotide Query, GenBank Accession No. AA680243, from Hillier, L. et al. (Dec. 1997).

NCBI Entrez Nucleotide Query, GenBank Accession No. AA610491, from NCI–CGAP (Dec. 1997).

NCBI Entrez Nucleotide Query, GenBank Accession No. AA702605, from Hillier, L. et al. (Dec. 1997).

NCBI Entrez Nucleotide Query, GenBank Accession No. AA130647, from Hillier, L. et al. (Dec. 1997).

NCBI Entrez Nucleotide Query, GenBank Accession No. AA714331, from NCI–CGAP (Jan. 1998).

NCBI Entrez Nucleotide Query, GenBank Accession No. AA720702, from NCI–CGAP (Jan. 1998).

NCBI Entrez Nucleotide Query, GenBank Accession No. AA779783, from Hillier, L. et al. (Feb. 1998).

NCBI Entrez Nucleotide Query, GenBank Accession No. AA807583, from NCI–CGAP (Feb. 1998).

NCBI Entrez Nucleotide Query, GenBank Accession No. AA805841, from NCI–CGAP (Feb. 1998).

NCBI Entrez Nucleotide Query, GenBank Accession No. AA664604, from NCI–CGAP (Feb. 1998).

NCBI Entrez Nucleotide Query, GenBank Accession No. AA665021, from NCI–CGAP (Feb. 1998).

NCBI Entrez Nucleotide Query, GenBank Accession No. AA829065, from NCI–CGAP (Feb. 1998).

NCBI Entrez Nucleotide Query, GenBank Accession No. AA846568, from NCI–CGAP (Mar. 1998).

NCBI Entrez Nucleotide Query, GenBank Accession No. AA653139, from Hillier, L. et al. (Mar. 1998).

NCBI Entrez Nucleotide Query, GenBank Accession No. AA653612, from Hillier, L. et al. (Mar. 1998).

NCBI Entrez Nucleotide Query, GenBank Accession No. AA608520, from Hillier, L. et al. (Mar. 1998).

NCBI Entrez Nucleotide Query, GenBank Accession No. AA644090, from Hillier, L. et al. (Mar. 1998).

NCBI Entrez Nucleotide Query, GenBank Accession No. AA876147, from NCI–CGAP (Mar. 1998).

NCBI Entrez Nucleotide Query, GenBank Accession No. AA828676, from NCI–CGAP (Apr. 1998).

NCBI Entrez Nucleotide Query, GenBank Accession No. AA828856, from NCI–CGAP (Apr. 1998).

NCBI Entrez Nucleotide Query, GenBank Accession No. AA904211, from NCI–CGAP (Apr. 1998).

NCBI Entrez Nucleotide Query, Genbank Accession No. XO6364 and Y00696, from Witzmann (Aug. 1993).

NCBI Entrez Nucleotide Query, GenBank Accession No. N52479, from Hillier et al. (Feb. 1996).

NCBI Entrez Nucleotide Query, GenBank Accession No. 270280, from Burgess (Mar. 1998).

```
              10          20          30          40          50          60
  1 GCA GGC GCG CCG GAG CCG GCC CCG TAG CGT GCC ATG GCC TGC TAC ATC TAC CAG CTG CCC  60
  1                                             M   A   C   Y   I   Y   Q   L   P    9

70          80          90         100         110         120
 61 TCC TGG GTG CTG GAC GAC CTG TGC CGC AAC ATG GAC GCG CTC AGC GAG TGG GAC TGG ATG 120
 10  S   W   V   L   D   D   L   C   R   N   M   D   A   L   S   E   W   D   W   M   29

130         140         150         160         170         180
121 GAG TTC GCC TCC TAC GTG ATC ACA GAC CTG ACC CAG CTG CGG AAG ATC AAG TCC ATG GAG 180
 30  E   F   A   S   Y   V   I   T   D   L   T   Q   L   R   K   I   K   S   M   E   49

190         200         210         220         230         240
181 CGG GTG CAG GGT GTG AGC ATC ACG CGG GAG CTG CTG TGG TGG TGG GGC ATG CGG CAG GCC 240
 50  R   V   Q   G   V   S   I   T   R   E   L   L   W   W   W   G   M   R   Q   A   69

250         260         270         280         290         300
241 ACC GTC CAG CAA CTT GTG GAC CTC CTG TGC CGC CTG GAG CTC TAC CGG GCT GCC CAG ATC 300
 70  T   V   Q   Q   L   V   D   L   L   C   R   L   E   L   Y   R   A   A   Q   I   89

310         320         330         340         350         360
301 ATC CTG AAC TGG AAA CCG GCT CCT GAA ATC AGG TGT CCC ATT CCA GCC TTC CCT GAC TCT 360
 90  I   L   N   W   K   P   A   P   E   I   R   C   P   I   P   A   F   P   D   S  109

370         380         390         400         410         420
361 GTG AAG CCA GAA AAG CCT TTG GCA GCT TCT GTA AGA AAG GCT GAG GAT GAA CAG GAA GAG 420
110  V   K   P   E   K   P   L   A   A   S   V   R   K   A   E   D   E   Q   E   E  129

430         440         450         460         470         480
421 GGG CAG CCT GTG AGG ATG GCC ACC TTT CCA GGC CCA GGG TCC TCT CCA GCC AGA GCC CAC 480
130  G   Q   P   V   R   M   A   T   F   P   G   P   G   S   S   P   A   R   A   H  149

490         500         510         520         530         540
481 CAG CCG GCC TTT CTC CAG CCT CCT GAA GAA GAT GCC CCT CAT TCC TTG AGA AGC GAC CTC 540
150  Q   P   A   F   L   Q   P   P   E   E   D   A   P   H   S   L   R   S   D   L  169

550         560         570         580         590         600
541 CCC ACT TCG TCT GAT TCA AAG GAC TTC AGC ACC TCC ATT CCT AAG CAG GAA AAA CTT TTG 600
170  P   T   S   S   D   S   K   D   F   S   T   S   I   P   K   Q   E   K   L   L  189

610         620         630         640         650         660
601 AGC TTG GCT GGA GAC AGC CTT TTC TGG AGT GAG GCA GAC GTG GTC CAG GCA ACC GAT GAC 660
190  S   L   A   G   D   S   L   F   W   S   E   A   D   V   V   Q   A   T   D   D  209
```

FIG. 1A

```
                      670         680         690         700         710         720
661  TTC AAT CAA AAC CGC AAA ATC AGC CAG GGG ACC TTT GCT GAC GTC TAC AGA GGG CAC AGG  720
210   F   N   Q   N   R   K   I   S   Q   G   T   F   A   D   V   Y   R   G   H   R   229

730         740         750         760         770         780
721  CAC GGG AAG CCA TTC GTC TTC AAG AAG CTC AGA GAG ACA GCC TGT TCA AGT CCA GGA TCA  780
230   H   G   K   P   F   V   F   K   K   L   R   E   T   A   C   S   S   P   G   S   249

790         800         810         820         830         840
781  ATC GAA AGA TTC TTC CAG GCA GAG TTG CAG ATT TGT CTT AGA TGC TGC CAC CCC AAT GTC  840
250   I   E   R   F   F   Q   A   E   L   Q   I   C   L   R   C   C   H   P   N   V   269

850         860         870         880         890         900
841  TTA CCT GTG CTG GGC TTC TGT GCT GCA AGA CAG TTT CAC AGC TTC ATC TAC CCC TAC ATG  900
270   L   P   V   L   G   F   C   A   A   R   Q   F   H   S   F   I   Y   P   Y   M   289

910         920         930         940         950         960
901  GCA AAT GGT TCC CTA CAG GAC AGA CTG CAG GGT CAG GGT GGC TCG GAA CCC CTC CCC TGG  960
290   A   N   G   S   L   Q   D   R   L   Q   G   Q   G   G   S   E   P   L   P   W   309

970         980         990         1000        1010        1020
961  CCC CAG CGT GTC AGC ATC TGC TCA GGG CTG CTC TGT GCC GTC GAG TAC CTG CAT GGT CTG  1020
310   P   Q   R   V   S   I   C   S   G   L   L   C   A   V   E   Y   L   H   G   L   329

1030        1040        1050        1060        1070        1080
1021 GAG ATC ATC CAC AGC AAC GTC AAG AGC TCT AAT GTC TTG CTG GAC CAA AAT CTC ACC CCC  1080
330   E   I   I   H   S   N   V   K   S   S   N   V   L   L   D   Q   N   L   T   P   349

1090        1100        1110        1120        1130        1140
1081 AAA CTT GCT CAC CCA ATG GCT CAT CTG TGT CCT GTC AAC AAA AGG TCA AAA TAC ACC ATG  1140
350   K   L   A   H   P   M   A   H   L   C   P   V   N   K   R   S   K   Y   T   M   369

1150        1160        1170        1180        1190        1200
1141 ATG AAG ACT CAC CTG CTC CGG ACG TCA GCC GCG TAT CTG CCA GAG GAT TTC ATC CGG GTG  1200
370   M   K   T   H   L   L   R   T   S   A   A   Y   L   P   E   D   F   I   R   V   389

1210        1220        1230        1240        1250        1260
1201 GGG CAG CTG ACA AAG CGA GTG GAC ATC TTC AGC TGT GGA ATA GTG TTG GCC GAG GTC CTC  1260
390   G   Q   L   T   K   R   V   D   I   F   S   C   G   I   V   L   A   E   V   L   409

1270        1280        1290        1300        1310        1320
1261 ACG GGC ATC CCT GCA ATG GAT AAC AAC CGA AGC CCG GTT TAC CTG AAG GAC TTA CTC CTC  1320
410   T   G   I   P   A   M   D   N   N   R   S   P   V   Y   L   K   D   L   L   L   429
```

FIG. 1B

```
          1330      1340      1350      1360      1370      1380
1321 AGT GAA ATT CCA AGC AGC ACC GCC TCG CTC TGC TCC AGG AAG ACG GGC GTG GAG AAC GTG 1380
430   S   E   I   P   S   S   T   A   S   L   C   S   R   K   T   G   V   E   N   V  449
          1390      1400      1410      1420      1430      1440
1381 ATG GCA AAG GAG ATC TGC CAG AAG TAC CTG GAG AAG GGC GCA GGG AGG CTT CCG GAG GAC 1440
450   M   A   K   E   I   C   Q   K   Y   L   E   K   G   A   G   R   L   P   E   D  469
          1450      1460      1470      1480      1490      1500
1441 TGC GCC GAG GCC CTG GCC ACG GCT GCC TGC CTG TGC CTG CGG AGG CGT AAC ACC AGC CTG 1500
470   C   A   E   A   L   A   T   A   A   C   L   C   L   R   R   R   N   T   S   L  489
          1510      1520      1530      1540      1550      1560
1501 CAG GAG GTG TGT GGC TCT GTG GCT GCT GTG GAA GAG CGG CTC CGA GGT CGG GAG ACG TTG 1560
490   Q   E   V   C   G   S   V   A   A   V   E   E   R   L   R   G   R   E   T   L  509
          1570      1580      1590      1600      1610      1620
1561 CTC CCT TGG AGT GGG CTT TCT GAG GGT ACA GGC TCT TCT TCC AAC ACC CCA GAG GAA ACA 1620
510   L   P   W   S   G   L   S   E   G   T   G   S   S   S   N   T   P   E   E   T  529
          1630      1640      1650      1660      1670      1680
1621 GAC GAC GTT GAC AAT TCC AGC CTT GAT GCC TCC TCC TCC ATG AGT GTG GCA CCC TGG GCA 1680
530   D   D   V   D   N   S   S   L   D   A   S   S   S   M   S   V   A   P   W   A  549
          1690      1700      1710      1720      1730      1740
1681 GGG GCT GCC ACC CCA CTT CTC CCC ACA GAG AAT GGG GAA GGA AGG CTG CGG GTC ATC GTG 1740
550   G   A   A   T   P   L   L   P   T   E   N   G   E   G   R   L   R   V   I   V  569
          1750      1760      1770      1780      1790      1800
1741 GGA AGG GAG GCT GAC TCC TCC TCT GAG GCC TGT GTT GGC CTG GAG CCT CCC CAG GAT GTT 1800
570   G   R   E   A   D   S   S   S   E   A   C   V   G   L   E   P   P   Q   D   V  589
1801 ACA TAA 1806
590   T   *  590
```

FIG. 1C

|     | 10  |     |     | 20  |     |     | 30  |     |     | 40  |     |     | 50  |     |     | 60  |     |     |
|---|---|---|---|---|---|---|---|---|---|---|---|---|---|---|---|---|---|---|
| 1 | GCA | GGC | GCG | CCG | GAG | CCG | GCC | CCG | TAG | CGT | GCC | ATG | GCC | TGC | TAC | ATC | TAC | CAG | CTG | CCC | 60 |
| 1 |     |     |     |     |     |     |     |     |     |     |     | M   | A   | C   | Y   | I   | Y   | Q   | L   | P   | 9 |

```
                10              20              30              40              50              60
  1 GCA GGC GCG CCG GAG CCG GCC CCG TAG CGT GCC ATG GCC TGC TAC ATC TAC CAG CTG CCC  60
  1                                              M   A   C   Y   I   Y   Q   L   P    9
                70              80              90             100             110             120
 61 TCC TGG GTG CTG GAC GAC CTG TGC CGC AAC ATG GAC GCG CTC AGC GAG TGG GAC TGG ATG 120
 10  S   W   V   L   D   D   L   C   R   N   M   D   A   L   S   E   W   D   W   M   29
               130             140             150             160             170             180
121 GAG TTC GCC TCC TAC GTG ATC ACA GAC CTG ACC CAG CTG CGG AAG ATC AAG TCC ATG GAG 180
 30  E   F   A   S   Y   V   I   T   D   L   T   Q   L   R   K   I   K   S   M   E   49
               190             200             210             220             230             240
181 CGG GTG CAG GGT GTG AGC ATC ACG CGG GAG CTG CTG TGG TGG TGG GGC ATG CGG CAG GCC 240
 50  R   V   Q   G   V   S   I   T   R   E   L   L   W   W   W   G   M   R   Q   A   69
               250             260             270             280             290             300
241 ACC GTC CAG CAA CTT GTG GAC CTC CTG TGC CGC CTG GAG CTC TAC CGG GCT GCC CAG ATC 300
 70  T   V   Q   Q   L   V   D   L   L   C   R   L   E   L   Y   R   A   A   Q   I   89
               310             320             330             340             350             360
301 ATC CTG AAC TGG AAA CCG GCT CCT GAA ATC AGG TGT CCC ATT CCA GCC TTC CCT GAC TCT 360
 90  I   L   N   W   K   P   A   P   E   I   R   C   P   I   P   A   F   P   D   S  109
               370             380             390             400             410             420
361 GTG AAG CCA GAA AAG CCT TTG GCA GCT TCT GTA AGA AAG GCT GAG GAT GAA CAG GAA GAG 420
110  V   K   P   E   K   P   L   A   A   S   V   R   K   A   E   D   E   Q   E   E  129
               430             440             450             460             470             480
421 GGG CAG CCT GTG AGG ATG GCC ACC TTT CCA GGC CCA GGG TCC TCT CCA GCC AGA GCC CAC 480
130  G   Q   P   V   R   M   A   T   F   P   G   P   G   S   S   P   A   R   A   H  149
               490             500             510             520             530             540
481 CAG CCG GCC TTT CTC CAG CCT CCT GAA GAA GAT GCC CCT CAT TCC TTG AGA AGC GAC CTC 540
150  Q   P   A   F   L   Q   P   P   E   E   D   A   P   H   S   L   R   S   D   L  169
               550             560             570             580             590             600
541 CCC ACT TCG TCT GAT TCA AAG GAC TTC AGC ACC TCC ATT CCT AAG CAG GAA AAA CTT TTG 600
170  P   T   S   S   D   S   K   D   F   S   T   S   I   P   K   Q   E   K   L   L  189
               610             620             630             640             650             660
601 AGC TTG GCT GGA GAC AGC CTT TTC TGG AGT GAG GCA GAC GTG GTC CAG GCA ACC GAT GAC 660
190  S   L   A   G   D   S   L   F   W   S   E   A   D   V   V   Q   A   T   D   D  209
               670             680             690             700             710             720
661 TTC AAT CAA AAC CGC AAA ATC AGC CAG GGG ACC TTT GCT GAC GTC TAC AGA GGG CAC AGG 720
210  F   N   Q   N   R   K   I   S   Q   G   T   F   A   D   V   Y   R   G   H   R  229
               730             740             750             760             770             780
721 CAC GGG AAG CCA TTC GTC TTC AAG AAG CTC AGA GAG ACA GCC TGT TCA AGT CCA GGA TCA 780
230  H   G   K   P   F   V   F   K   K   L   R   E   T   A   C   S   S   P   G   S  249
               790             800             810             820             830             840
781 ATC GAA AGA TTC TTC CAG GCA GAG TTG CAG ATT TGT CTT AGA TGC TGC CAC CCC AAT GTC 840
250  I   E   R   F   F   Q   A   E   L   Q   I   C   L   R   C   C   H   P   N   V  269
```

FIG. 2A

```
                  850          860          870          880          890          900
 841 TTA CCT GTG CTG GGC TTC TGT GCT GCA AGA CAG TTT CAC AGC TTC ATC TAC CCC TAC ATG 900
 270  L   P   V   L   G   F   C   A   A   R   Q   F   H   S   F   I   Y   P   Y   M  289
                  910          920          930          940          950          960
 901 GCA AAT GGT TCC CTA CAG GAC AGA CTG CAG GGT CAG GGT GGC TCG GAC CCC CTC CCC TGG 960
 290  A   N   G   S   L   Q   D   R   L   Q   G   Q   G   G   S   D   P   L   P   W  309
                  970          980          990         1000         1010         1020
 961 CCC CAG CGT GTC AGC ATC TGC TCA GGG CTG CTC TGT GCC GTC GAG TAC CTG CAT GGT CTG 1020
 310  P   Q   R   V   S   I   C   S   G   L   L   C   A   V   E   Y   L   H   G   L  329
                 1030         1040         1050         1060         1070         1080
1021 GAG ATC ATC CAC AGC AAC GTC AAG AGC TCT AAT GTC TTG CTG GAC CAA AAT CTC ACC CCC 1080
 330  E   I   I   H   S   N   V   K   S   S   N   V   L   L   D   Q   N   L   T   P  349
                 1090         1100         1110         1120         1130         1140
1081 AAA CTT GCT CAC CCA ATG GCT CAT CTG TGT CCT GTC AAC AAA AGG TCA AAA TAC ACC ATG 1140
 350  K   L   A   H   P   M   A   H   L   C   P   V   N   K   R   S   K   Y   T   M  369
                 1150         1160         1170         1180         1190         1200
1141 ATG AAG ACT CAC CTG CTC CGG ACG TCA GCC GCG TAT CTG CCA GAG GAT TTC ATC CGG GTG 1200
 370  M   K   T   H   L   L   R   T   S   A   A   Y   L   P   E   D   F   I   R   V  389
                 1210         1220         1230         1240         1250         1260
1201 GGG CAG GTG ACA AAG CGA GTG GAC ATC TTC AGC TGT GGA ATA GTG TTG GCC GAG GTC CTC 1260
 390  G   Q   V   T   K   R   V   D   I   F   S   C   G   I   V   L   A   E   V   L  409
                 1270         1280         1290         1300         1310         1320
1261 ACG GGC ATC CCT GCA ATG GAT AAC AAC CGA AGC CCG GTT TAC CTG AAG GAC TTA CTC CTC 1320
 410  T   G   I   P   A   M   D   N   N   R   S   P   V   Y   L   K   D   L   L   L  429
                 1330         1340         1350         1360         1370         1380
1321 AGT GAA ATT CCA AGC AGC ACC GCC TCG CTC TGC TCC AGG AAG ACG GGC GTG GAG AAC GTG 1380
 430  S   E   I   P   S   S   T   A   S   L   C   S   R   K   T   G   V   E   N   V  449
                 1390         1400         1410         1420         1430         1440
1381 ATG GCA AAG GAG ATC TGC CAG AAG TAC CTG GAG AAG GGC GCA GGG AGG CTT CCG GAG GAC 1440
 450  M   A   K   E   I   C   Q   K   Y   L   E   K   G   A   G   R   L   P   E   D  469
                 1450         1460         1470         1480         1490         1500
1441 TGC GCC GAG GCC CTG GCC ACG GCT GCC TGC CTG TGC CTG CGG AGG CGT AAC ACC AGC CTG 1500
 470  C   A   E   A   L   A   T   A   A   C   L   C   L   R   R   R   N   T   S   L  489
                 1510         1520         1530         1540         1550         1560
1501 CAG GAG GTG TGT GGC TCT GTG GCT GCT GTG GAA GAG CGG CTC CGA GGT CGG GAG ACG TTG 1560
 490  Q   E   V   C   G   S   V   A   A   V   E   E   R   L   R   G   R   E   T   L  509
                 1570         1580         1590         1600         1610         1620
1561 CTC CCT TGG AGT GGG CTT TCT GAG GGT ACA GGC TCT TCT TCC AAC ACC CCA GAG GAA ACA 1620
 510  L   P   W   S   G   L   S   E   G   T   G   S   S   S   N   T   P   E   E   T  529
                 1630         1640         1650         1660         1670         1680
1621 GAC GAC GTT GAC AAT TCC AGC TTG GAT GCC TCC TCC TCC ATG AGT GTG GCA CCC TGG GCA 1680
 530  D   D   V   D   N   S   S   L   D   A   S   S   S   M   S   V   A   P   W   A  549
```

FIG. 2B

```
            1690        1700        1710        1720        1730        1740
1681 GGG GCT GCC ACC CCA CTT CTC CCC ACA GAG AAT GGG GAA GGA AGG CTG CGG GTC ATC GTG 1740
550   G   A   A   T   P   L   L   P   T   E   N   G   E   G   R   L   R   V   I   V  569
            1750        1760        1770        1780        1790        1800
1741 GGA AGG GAG GCT GAC TCC TCC TCT GAG GCC TGT GTT GGC CTG GAG CCT CCC CAG GAT GTT 1800
570   G   R   E   A   D   S   S   S   E   A   C   V   G   L   E   P   P   Q   D   V  589
            1810        1820        1830        1840        1850        1860
1801 ACA GAA ACT TCG TGG CAA ATT GAG ATC AAT GAG GCC AAA AGG AAA CTG ATG GAG AAT ATT 1860
590   T   E   T   S   W   Q   I   E   I   N   E   A   K   R   K   L   M   E   N   I  609
            1870        1880        1890        1900        1910        1920
1861 CTG CTC TAC AAA GAG GAA AAA GTG GAC AGC ATT GAG CTC TTT GGC CCC TGA TGA CCG GAA 1920
610   L   L   Y   K   E   E   K   V   D   S   I   E   L   F   G   P   *               625
            1930        1940        1950        1960        1970        1980
1921 CAC AGC TGA GGA CCC TTG TCC TCA GTT GGA AAG ATG AGC ATC AGA TCA GAA AGG TCT 1980
            1990        2000        2010        2020        2030        2040
1981 GAG GCA GAA TCC AAG ATC TGC CAG GAA ACA CAC AAC AAA ACA TCT GCT GTC CTG GGT GGG 2040
            2050        2060        2070        2080        2090        3000
2041 AGG GAA ACT TCA TTT CAC TGG AAT GAG TTG GGA GAG AAA GGC CCT CAG CTT TTA GAG ACA 2100
            2110        2120        2130        2140        2150        2160
2101 CAA AAA TCC ATG AAG TCT CTT CCT TTC TGG GCT TTG TTA GTC AGA GCA GGG GAT CAG AGG 2160
            2170        2180        2190        2200        2210        2220
2161 AGA CTG AAG CAG AAA CCC TGC ACA CGG GCC CAG GAT GTG GCT GAT TTT GTG GTT CCG GGG 2220
            2230        2240        2250        2260        2270        2280
2221 AGT ATG TGA TGA TAA TCA CCC CCA GCA GAT TCC ATT ACC TCA GCA GCT CTT GTT CCC CCG 2280
            2290        2300        2310        2320        2330        2340
2281 CCA CTG GCA GTT CTG CAA TGC CAT AGC ATT TTC CAG AGC TAA GAT CTC TGG GTT GTA TTT 2340
            2350        2360        2370        2380        2390        2400
2341 GCT GAC AGC CTG CAA GCT TGC ATG CTC TGA AAG ATT TTT TTA GTT TTT AAT TTT TTT GTA 2400
            2410        2420        2430        2440        2450        2460
2401 AAA ATG GGG TCT CGC TTT GTT GGC GCA ATC CTC CCA CCT CAG ACT CCC AAA GTG CTG GAA 2460
            2470        2480        2490        2500        2510        2520
2461 TTA CAT TGG GAA CCA CTG TGC CTG GCC TGG AAA ACT TCC AAC TTG TGT TCT CAG TGC AGT 2520
            2530        2540        2550        2560        2570        2580
2521 TCT GAC TCA CCT CTC TGG GCC TCA GGT TCT ACA AAT GCC AGA CAC CTA GCG AAG AGC TCT 2580
            2590        2600        2610        2620        2630        2640
2581 GCA GGC TTT CCA CTG CCT GTA TTG GAA ATC TTG CAA TTC ACA TAA TTA TTC AGT CAC TGC 2640
            2650        2660        2670        2680        2690        2700
2641 CTG GTA CCT TTA TCT TCC CAT CCC ATT AAT GTT AGT GTT TTT AAA TGG AGC TTT TAT TCT 2700
            2710        2720        2730        2740        2750        2760
2701 GAG AAT ATG TGT TCG TCT GTT TGT TTG TTT TTT GAG ACA GAG TCT CAC TTT GTC ACC CAG 2760
            2770        2780        2790        2800        2810        2820
2761 GCT GGA GTG CAG TGG CAC GAT CTC AGC TCA CTG CAA GCT GTG CCT CTC AGG TTT CAA GTG 2820
```

FIG. 2C

```
      2830        2840        2850        2860        2870        2880
2821 ATT CTC CTG CCT CAG CCT CCT GAG TAG ATG GGA CTG TAG GCA CCT GCC ACT ATG CCT GGC 2880
      2890        2900        2910        2920        2930        2940
2881 TAA TTT TTG TGT TTT TAG TAG AGA CAG GGT TTC ACC ATA TTG CCA GGG CTG GTC TCG AAC 2940
      2950        2960        2970        2980        2990        3000
2941 TAC TGA CCT CGT GAT CTG CCC GCC TTG GCC TAT CAA AGT GTT GGG ATT ACA GGC TTG AGC 3000
      3010        3020        3030        3040        3050        3060
3001 CAC CGC ACC CGG CCG AGA ATA TGT GTT GTT ATT TAT GAC TGG ATT ATG AAG AAT CAG GAG 3060
      3070        3080        3090        3100        3110        3120
3061 AAT GCA TTT CAT GTC TGA TTC TGC TGC TAA TTA AGT CAA TCA TTT AAT TTT TGG GAC CTC 3120
      3130        3140        3150        3160        3170        3180
3121 AGT TTC TTT GTA AGT AAA ATA ACA CCT GCT TGT TCT TCA TCC CTG GGC TGT TGG GAG GAA 3180
      3190        3200        3210        3220        3230        3240
3181 CAG ATG AGA CAG TGG CTA TAG AAG CAC TTG GAA AAT GCA CTT GTC CTG TTT TGT AAA ATA 3240
      3250        3260        3270        3280        3290        3300
3241 AAA AGG TAT TAA ATG TGT ATT TCT GCC ATG TAC CTA ATG ATT ATT CAG TGC GTA TAT ATC 3300
      3310        3320        3330        3340        3350        3360
3301 TGA AAA GTC ATG TTG CAA ATC TTT CTG TGA AAC AGA TGC TAT TTT AAA TTC ACT GGG AGA 3360
      3370        3380        3390        3400        3410        3420
3361 AAT ATC CTA TTT AAA GTA ATC TAT AGT AAT TTC TTT TTA TAT AAT AAA AAT ATA TTT GTA 3420
      3430        3440        3450
3421 AAG TCG AAA AAA AAA AAA AAA AAA AAA AAA AAA AAA AAA     3459
```

FIG. 2D

```
  1 MAGGPGPGEPAAPGAG----------HFLYEVPPNVM-----CRFYKVMD   IRAK
  1 MSGVQTAEAEAQAQNDANGNRTRSRSHLDNTMAIRLLPLPVRAQLCAHLQ   Pelle
  1 MAC---------------------YIYQLPSWVL-----DDLCRNMD     HNFIP11X IRAK-2 Alpha
  1 MAC---------------------YIYQLPSWVL-----DDLCRNMD     HNFIP11XX IRAK-2 Beta 36 ALEPADWCQFAALIVRDQTELRLCERSGQRTASM------LWPAINR-NA   IRAK
 51 ALDV--AQQLATAVKLYPDVEQISSQKQR--GRSASNEFLNIAGGQYNH    Pelle
 22 ALSEWDWMEFASYVITDLTQLRKI-KSMERVQGVSITRELLWWWGMR-QA   HNFIP11X IRAK-2 Alpha
 22 ALSEWDWMEFASYVITDLTQLRKI-KSMERVQGVSITRELLWWWGMR-QA   HNFIP11XX IRAK-2 Beta 79 RVADLVHILTHLQLLRARDIITAAHPPAPLPSDGTTAPRPSSIPAPAEAE   IRAK
 97 TVQTLFALFKKLKHNAMRLIKDYVSED--------LHKYIPRSVPTISE    Pelle
 70 TVQQLVDLLCRLELYRAAQIILNWKPAPEIRCPIPAFPDSVKPEKPLAAS   HNFIP11X IRAK-2 Alpha
 70 TVQQLVDLLCRLELYRAAQIILNWKPAPEIRCPIPAFPDSVKPEKPLAAS   HNFIP11X IRAK-2 Beta 129 AWSPRKLPSSASTFLSPAFPGSQTHSGPELG---LVPS----PASLWPPP   IRAK
139 LRAAPD--SSAKVNNGPPFPSSSGVSNSNNNRTSTTATEEIPSLE-----   Pelle
120 VRKAEDEQEEGQPVRMATFPGPGSSPARAHQPAFLQPPEEDAPHSLRSDL   HNFIP11X IRAK-2 Alpha
120 VRKAEDEQEEGQPVRMATFPGPGSSPARAHQPAFLQPPEEDAPHSLRSDL   HNFIP11X IRAK-2 Beta 172 PSPAPSSTKPGPESSVSLLQGARPSPFCAPLCEISRGTHNFSEELKIGEG   IRAK
182 --SLGNIHISTVQRAAESLLEID-------YAELENATDGWSPDNRLGQG   Pelle
170 PTSSDSKDFSTSIPKQEKLLSLAGDSLFWSEADVVQATDDFNQNRKISQG   HNFIP11X IRAK-2 Alpha
170 PTSSDSKDFSTSIPKQEKLLSLAGDSLFWSEADVVQATDDFNQNRKISQG   HNFIP11X IRAK-2 Beta 222 GFGCVYRAVMRNTVYAVKRLK---ENADLEWTAVKQSFLTEVEQLSRFRH   IRAK
223 GFGDVYRGKWKQLDVAIKVMNYRSPNIDQKMVELQQSYN-ELKYLNSIRH   Pelle
220 TFADVYRGHRHGKPFVFKKLR---ETACSSPGSIERFFQAELQICLRCCH   HNFIP11X IRAK-2 Alpha
220 TFADVYRGHRHGKPFVFKKLR---ETACSSPGSIERFFQAELQICLRCCH   HNFIP11X IRAK-2 Beta 269 PNIVDFAGYCAQNGFYCLVYGFLPNGSLEDRLHCQTQACP--PLSWPQRL   IRAK
272 DNILALYGYSIKGQKPCLVYQLMKGGSLEARLRAHKAQNPLPALTAQQRF   Pelle
267 PNVLPVLGFCAARQFHSFIYPYMANGSLQDRLQGQG-GSE--PLPWPQRV   HNFIP11X IRAK-2 Alpha
267 PNVLPVLGFCAARQFHSFIYPYMANGSLQDRLQGQG-GSD--PLPWPQRV   HNFIP11X IRAK-2 Beta 317 DILLGTARAIQFLHQD-SPSLIHGDIKSSNVLLDERLTPKLGDFGLARFS   IRAK
322 SISLGTARGIYFLHTARCTPLIHGDIKPANILLDQCLQPKIGDFGLVR--   Pelle
314 SICSGLLCAVEYLH---GLEIIHSNVKSSNVLLDQNLTPKLAH-PMAHLC   HNFIP11X IRAK-2 Alpha
314 SICSGLLCAVEYLH---GLEIIHSNVKSSNVLLDQNLTPKLAH-PMAHLC   HNFIP11X IRAK-2 Beta 366 RFAGSSPSQSSMVARTQTVRGTLAYLPLEYIKTGRLAVDTDTFSFGVVVL   IRAK
370 ----EGPKSLDAVVEVNKVFGTKIYLPPEFRNFRQLSTGVDVYSFGIVLL   Pelle
360 --PVNKRSKYTMM-KTHLLRTSAAYLPEDFIRVGQLTKRVDIFSCGIVLA   HNFIP11X IRAK-2 Alpha
360 --PVNKRSKYTMM-KTHLLRTSAAYLPEDFIRVGQVTKRVDIFSCGIVLA   HNFIP11X IRAK-2 Beta
```

FIG.3A

```
416  ETLAGQRAVKTHGARTKYLKDLVEEEAEEAGVALRSTQSTLQAGLAADAK         IRAK
416  EVFTG-RQVTDRVPENETKKNLLD--------------------YVKQQA         Pelle
407  EVLTGIPAMDNNRSPV-YLKDLLLSEIPSSTASLCSRKTGVENVMAKE--         HNFIP11X IRAK-2 Alpha
407  EVLTGIPAMDNNRSPV-YLKDLLLSEIPSSTASLCSRKTGVENVMAKE--         HNFIP11X IRAK-2 Beta 466  AAPIAMQIYKKHLDPRPGPCPPELGLGLGQLACCCLHRRAKRRPPMTQVY         IRAK
445  RQNR-MELLEKHLAAPMGK-------ELDM--CMC--------------         Pelle
454  -------ICQKYLEKGAGRLPEDCAEALATAACLCLRRRNTS--------         HNFIP11X IRAK-2 Alpha
454  -------ICQKYLEKGAGRLPEDCAEALATAACLCLRRRNTS--------         HNFIP11X IRAK-2 Beta 516  ERLEKLQAVVAGVPGHLEAASCIPPSPQENSYVSSTGRAHSGAAPWQPLA         IRAK
470  ----------AIEAGLH--------------------------------         Pelle
489  --LQEVCGSVAAVEERL--------------------RGRETLLPWSGLS         HNFIP11X IRAK-2 Alpha
489  --LQEVCGSVAAVEERL--------------------RGRETLLPWSGLS         HNFIP11X IRAK-2 Beta 566  APSGASAQAAEQLQRGPNQPVESDESLGGLSAALRSAHLTPSCPLDPAPL         IRAK
477  -------------------------------------------------         Pelle
517  EGTGSSSNTPEETDDVDNSSLDASSSMS-----VAPWA-GAATPLLPT--         HNFIP11X IRAK-2 Alpha
517  EGTGSSSNTPEETDDVDNSSLDASSSMS-----VAPWA-GAATPLLPT--         HNFIP11X IRAK-2 Beta 616  REAGCPQGDTAGESSWGSGPGSRPTAVEGLALGSSASSSSEPPQIIINPA         IRAK
477  ----------------------------CTALDPQDR----------PS         Pelle
559  -------ENGEGRLRVIVGREADSSSEACVGLEPPQDVT            HNFIP11X IRAK-2 Alpha
559  -------ENGEGRLRVIVGREADSSSEACVGLEPPQDVTETSWQIEINEA         HNFIP11X IRAK-2 Beta 666  RQKMVQKLALYEDGALDSLQLLSSSSLPGLGLEQDRQGPEESDEFQS            IRAK4
488  MNAVLKRFEPFVTD                                            Pelle
591                                                            HNFIP11X IRAK-2 Alpha
602  KRKLMENILLYKEEKVDSIELFGP                                  HNFIP11X IRAK-2 Beta
```

FIG.3B

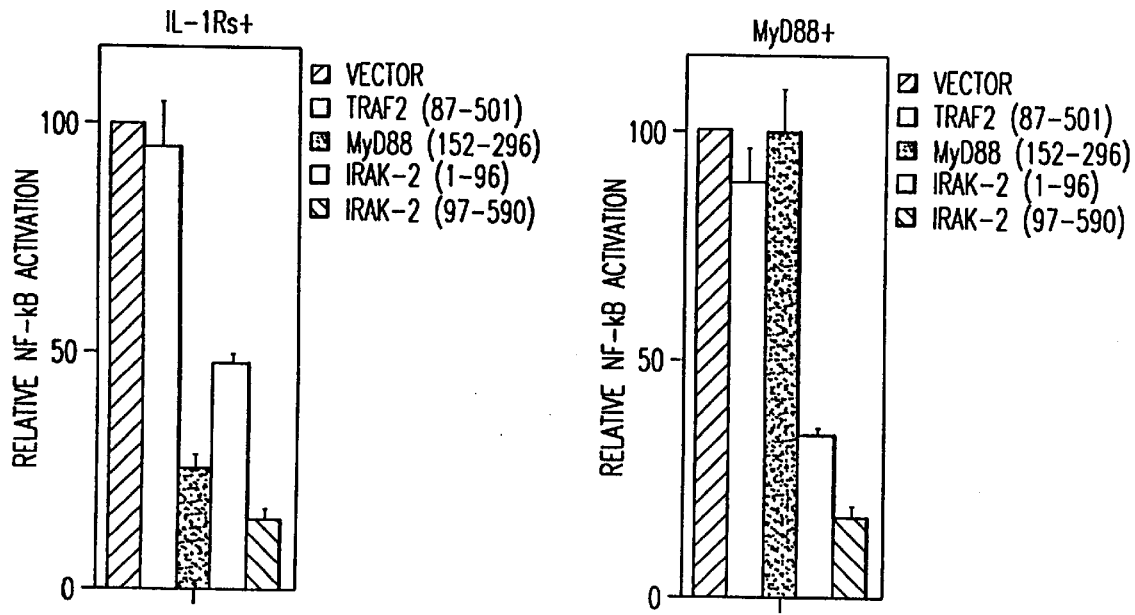
FIG. 8A
FIG. 8B
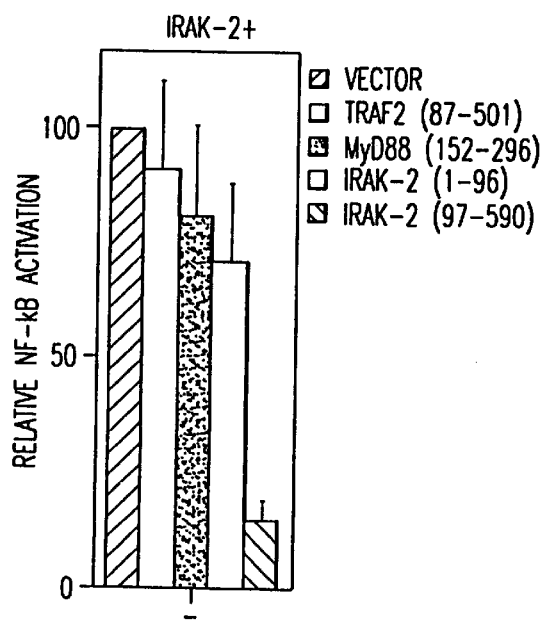
FIG. 8C

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 1806 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 34..1803

(xi) SEQUENCE DESCRIPTION: SEQ ID NO:1:

```
GCAGGCGCGC CGGAGCCGGC CCCGTAGCGT GCC ATG GCC TGC TAC ATC TAC CAG         54
                                  Met Ala Cys Tyr Ile Tyr Gln
                                   1               5

CTG CCC TCC TGG GTG CTG GAC GAC CTG TGC CGC AAC ATG GAC GCG CTC         102
Leu Pro Ser Trp Val Leu Asp Asp Leu Cys Arg Asn Met Asp Ala Leu
         10                  15                  20

AGC GAG TGG GAC TGG ATG GAG TTC GCC TCC TAC GTG ATC ACA GAC CTG         150
Ser Glu Trp Asp Trp Met Glu Phe Ala Ser Tyr Val Ile Thr Asp Leu
     25                  30                  35

ACC CAG CTG CGG AAG ATC AAG TCC ATG GAG CGG GTG CAG GGT GTG AGC         198
Thr Gln Leu Arg Lys Ile Lys Ser Met Glu Arg Val Gln Gly Val Ser
 40                  45                  50                  55

ATC ACG CGG GAG CTG CTG TGG TGG TGG GGC ATG CGG CAG GCC ACC GTC         246
Ile Thr Arg Glu Leu Leu Trp Trp Trp Gly Met Arg Gln Ala Thr Val
                 60                  65                  70

CAG CAA CTT GTG GAC CTC CTG TGC CGC CTG GAG CTC TAC CGG GCT GCC         294
Gln Gln Leu Val Asp Leu Leu Cys Arg Leu Glu Leu Tyr Arg Ala Ala
             75                  80                  85

CAG ATC ATC CTG AAC TGG AAA CCG GCT CCT GAA ATC AGG TGT CCC ATT         342
Gln Ile Ile Leu Asn Trp Lys Pro Ala Pro Glu Ile Arg Cys Pro Ile
         90                  95                 100

CCA GCC TTC CCT GAC TCT GTG AAG CCA GAA AAG CCT TTG GCA GCT TCT         390
Pro Ala Phe Pro Asp Ser Val Lys Pro Glu Lys Pro Leu Ala Ala Ser
     105                 110                 115

GTA AGA AAG GCT GAG GAT GAA CAG GAA GAG GGG CAG CCT GTG AGG ATG         438
Val Arg Lys Ala Glu Asp Glu Gln Glu Glu Gly Gln Pro Val Arg Met
120                 125                 130                 135

GCC ACC TTT CCA GGC CCA GGG TCC TCT CCA GCC AGA GCC CAC CAG CCG         486
Ala Thr Phe Pro Gly Pro Gly Ser Ser Pro Ala Arg Ala His Gln Pro
                 140                 145                 150

GCC TTT CTC CAG CCT CCT GAA GAA GAT GCC CCT CAT TCC TTG AGA AGC         534
Ala Phe Leu Gln Pro Pro Glu Glu Asp Ala Pro His Ser Leu Arg Ser
             155                 160                 165

GAC CTC CCC ACT TCG TCT GAT TCA AAG GAC TTC AGC ACC TCC ATT CCT         582
```

```
Asp Leu Pro Thr Ser Ser Asp Ser Lys Asp Phe Ser Thr Ser Ile Pro
        170                 175                 180

AAG CAG GAA AAA CTT TTG AGC TTG GCT GGA GAC AGC CTT TTC TGG AGT        630
Lys Gln Glu Lys Leu Leu Ser Leu Ala Gly Asp Ser Leu Phe Trp Ser
        185                 190                 195

GAG GCA GAC GTG GTC CAG GCA ACC GAT GAC TTC AAT CAA AAC CGC AAA        678
Glu Ala Asp Val Val Gln Ala Thr Asp Asp Phe Asn Gln Asn Arg Lys
200                 205                 210                 215

ATC AGC CAG GGG ACC TTT GCT GAC GTC TAC AGA GGG CAC AGG CAC GGG        726
Ile Ser Gln Gly Thr Phe Ala Asp Val Tyr Arg Gly His Arg His Gly
                220                 225                 230

AAG CCA TTC GTC TTC AAG AAG CTC AGA GAG ACA GCC TGT TCA AGT CCA        774
Lys Pro Phe Val Phe Lys Lys Leu Arg Glu Thr Ala Cys Ser Ser Pro
                235                 240                 245

GGA TCA ATC GAA AGA TTC TTC CAG GCA GAG TTG CAG ATT TGT CTT AGA        822
Gly Ser Ile Glu Arg Phe Phe Gln Ala Glu Leu Gln Ile Cys Leu Arg
            250                 255                 260

TGC TGC CAC CCC AAT GTC TTA CCT GTG CTG GGC TTC TGT GCT GCA AGA        870
Cys Cys His Pro Asn Val Leu Pro Val Leu Gly Phe Cys Ala Ala Arg
        265                 270                 275

CAG TTT CAC AGC TTC ATC TAC CCC TAC ATG GCA AAT GGT TCC CTA CAG        918
Gln Phe His Ser Phe Ile Tyr Pro Tyr Met Ala Asn Gly Ser Leu Gln
280                 285                 290                 295

GAC AGA CTG CAG GGT CAG GGT GGC TCG GAA CCC CTC CCC TGG CCC CAG        966
Asp Arg Leu Gln Gly Gln Gly Gly Ser Glu Pro Leu Pro Trp Pro Gln
                300                 305                 310

CGT GTC AGC ATC TGC TCA GGG CTG CTC TGT GCC GTC GAG TAC CTG CAT       1014
Arg Val Ser Ile Cys Ser Gly Leu Leu Cys Ala Val Glu Tyr Leu His
                315                 320                 325

GGT CTG GAG ATC ATC CAC AGC AAC GTC AAG AGC TCT AAT GTC TTG CTG       1062
Gly Leu Glu Ile Ile His Ser Asn Val Lys Ser Ser Asn Val Leu Leu
            330                 335                 340

GAC CAA AAT CTC ACC CCC AAA CTT GCT CAC CCA ATG GCT CAT CTG TGT       1110
Asp Gln Asn Leu Thr Pro Lys Leu Ala His Pro Met Ala His Leu Cys
        345                 350                 355

CCT GTC AAC AAA AGG TCA AAA TAC ACC ATG ATG AAG ACT CAC CTG CTC       1158
Pro Val Asn Lys Arg Ser Lys Tyr Thr Met Met Lys Thr His Leu Leu
360                 365                 370                 375

CGG ACG TCA GCC GCG TAT CTG CCA GAG GAT TTC ATC CGG GTG GGG CAG       1206
Arg Thr Ser Ala Ala Tyr Leu Pro Glu Asp Phe Ile Arg Val Gly Gln
                380                 385                 390

CTG ACA AAG CGA GTG GAC ATC TTC AGC TGT GGA ATA GTG TTG GCC GAG       1254
Leu Thr Lys Arg Val Asp Ile Phe Ser Cys Gly Ile Val Leu Ala Glu
                395                 400                 405

GTC CTC ACG GGC ATC CCT GCA ATG GAT AAC AAC CGA AGC CCG GTT TAC       1302
Val Leu Thr Gly Ile Pro Ala Met Asp Asn Asn Arg Ser Pro Val Tyr
            410                 415                 420

CTG AAG GAC TTA CTC CTC AGT GAA ATT CCA AGC AGC ACC GCC TCG CTC       1350
Leu Lys Asp Leu Leu Leu Ser Glu Ile Pro Ser Ser Thr Ala Ser Leu
425                 430                 435

TGC TCC AGG AAG ACG GGC GTG GAG AAC GTG ATG GCA AAG GAG ATC TGC       1398
Cys Ser Arg Lys Thr Gly Val Glu Asn Val Met Ala Lys Glu Ile Cys
440                 445                 450                 455

CAG AAG TAC CTG GAG AAG GGC GCA GGG AGG CTT CCG GAG GAC TGC GCC       1446
Gln Lys Tyr Leu Glu Lys Gly Ala Gly Arg Leu Pro Glu Asp Cys Ala
                460                 465                 470

GAG GCC CTG GCC ACG GCT GCC TGC CTG TGC CTG CGG AGG CGT AAC ACC       1494
Glu Ala Leu Ala Thr Ala Ala Cys Leu Cys Leu Arg Arg Arg Asn Thr
                475                 480                 485
```

```
AGC CTG CAG GAG GTG TGT GGC TCT GTG GCT GCT GTG GAA GAG CGG CTC      1542
Ser Leu Gln Glu Val Cys Gly Ser Val Ala Ala Val Glu Glu Arg Leu
        490                 495                 500

CGA GGT CGG GAG ACG TTG CTC CCT TGG AGT GGG CTT TCT GAG GGT ACA      1590
Arg Gly Arg Glu Thr Leu Leu Pro Trp Ser Gly Leu Ser Glu Gly Thr
505                 510                 515

GGC TCT TCT TCC AAC ACC CCA GAG GAA ACA GAC GAC GTT GAC AAT TCC      1638
Gly Ser Ser Ser Asn Thr Pro Glu Glu Thr Asp Asp Val Asp Asn Ser
520                 525                 530                 535

AGC CTT GAT GCC TCC TCC TCC ATG AGT GTG GCA CCC TGG GCA GGG GCT      1686
Ser Leu Asp Ala Ser Ser Ser Met Ser Val Ala Pro Trp Ala Gly Ala
            540                 545                 550

GCC ACC CCA CTT CTC CCC ACA GAG AAT GGG GAA GGA AGG CTG CGG GTC      1734
Ala Thr Pro Leu Leu Pro Thr Glu Asn Gly Glu Gly Arg Leu Arg Val
            555                 560                 565

ATC GTG GGA AGG GAG GCT GAC TCC TCC TCT GAG GCC TGT GTT GGC CTG      1782
Ile Val Gly Arg Glu Ala Asp Ser Ser Ser Glu Ala Cys Val Gly Leu
            570                 575                 580

GAG CCT CCC CAG GAT GTT ACA TAA                                      1806
Glu Pro Pro Gln Asp Val Thr
585                 590
```

(2) INFORMATION FOR SEQ ID NO:2:

(i) SEQUENCE CHARACTERISTICS:
        (A) LENGTH: 590 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Cys Tyr Ile Tyr Gln Leu Pro Ser Trp Val Leu Asp Asp Leu
1               5                   10                  15

Cys Arg Asn Met Asp Ala Leu Ser Glu Trp Asp Trp Met Glu Phe Ala
                20                  25                  30

Ser Tyr Val Ile Thr Asp Leu Thr Gln Leu Arg Lys Ile Lys Ser Met
            35                  40                  45

Glu Arg Val Gln Gly Val Ser Ile Thr Arg Glu Leu Leu Trp Trp Trp
        50                  55                  60

Gly Met Arg Gln Ala Thr Val Gln Gln Leu Val Asp Leu Leu Cys Arg
65                  70                  75                  80

Leu Glu Leu Tyr Arg Ala Ala Gln Ile Ile Leu Asn Trp Lys Pro Ala
                85                  90                  95

Pro Glu Ile Arg Cys Pro Ile Pro Ala Phe Pro Asp Ser Val Lys Pro
            100                 105                 110

Glu Lys Pro Leu Ala Ala Ser Val Arg Lys Ala Glu Asp Glu Gln Glu
        115                 120                 125

Glu Gly Gln Pro Val Arg Met Ala Thr Phe Pro Gly Pro Gly Ser Ser
130                 135                 140

Pro Ala Arg Ala His Gln Pro Ala Phe Leu Gln Pro Glu Glu Asp
145                 150                 155                 160

Ala Pro His Ser Leu Arg Ser Asp Leu Pro Thr Ser Ser Asp Ser Lys
                165                 170                 175

Asp Phe Ser Thr Ser Ile Pro Lys Gln Glu Lys Leu Leu Ser Leu Ala
            180                 185                 190

Gly Asp Ser Leu Phe Trp Ser Glu Ala Asp Val Val Gln Ala Thr Asp
        195                 200                 205
```

-continued

```
Asp Phe Asn Gln Asn Arg Lys Ile Ser Gln Gly Thr Phe Ala Asp Val
    210                 215                 220

Tyr Arg Gly His Arg His Gly Lys Pro Phe Val Phe Lys Lys Leu Arg
225                 230                 235                 240

Glu Thr Ala Cys Ser Ser Pro Gly Ser Ile Glu Arg Phe Phe Gln Ala
                245                 250                 255

Glu Leu Gln Ile Cys Leu Arg Cys Cys His Pro Asn Val Leu Pro Val
            260                 265                 270

Leu Gly Phe Cys Ala Ala Arg Gln Phe His Ser Phe Ile Tyr Pro Tyr
        275                 280                 285

Met Ala Asn Gly Ser Leu Gln Asp Arg Leu Gln Gly Gln Gly Gly Ser
    290                 295                 300

Glu Pro Leu Pro Trp Pro Gln Arg Val Ser Ile Cys Ser Gly Leu Leu
305                 310                 315                 320

Cys Ala Val Glu Tyr Leu His Gly Leu Glu Ile Ile His Ser Asn Val
                325                 330                 335

Lys Ser Ser Asn Val Leu Leu Asp Gln Asn Leu Thr Pro Lys Leu Ala
            340                 345                 350

His Pro Met Ala His Leu Cys Pro Val Asn Lys Arg Ser Lys Tyr Thr
        355                 360                 365

Met Met Lys Thr His Leu Leu Arg Thr Ser Ala Ala Tyr Leu Pro Glu
    370                 375                 380

Asp Phe Ile Arg Val Gly Gln Leu Thr Lys Arg Val Asp Ile Phe Ser
385                 390                 395                 400

Cys Gly Ile Val Leu Ala Glu Val Leu Thr Gly Ile Pro Ala Met Asp
                405                 410                 415

Asn Asn Arg Ser Pro Val Tyr Leu Lys Asp Leu Leu Leu Ser Glu Ile
            420                 425                 430

Pro Ser Ser Thr Ala Ser Leu Cys Ser Arg Lys Thr Gly Val Glu Asn
        435                 440                 445

Val Met Ala Lys Glu Ile Cys Gln Lys Tyr Leu Glu Lys Gly Ala Gly
    450                 455                 460

Arg Leu Pro Glu Asp Cys Ala Glu Ala Leu Ala Thr Ala Ala Cys Leu
465                 470                 475                 480

Cys Leu Arg Arg Arg Asn Thr Ser Leu Gln Glu Val Cys Gly Ser Val
                485                 490                 495

Ala Ala Val Glu Glu Arg Leu Arg Gly Arg Glu Thr Leu Leu Pro Trp
            500                 505                 510

Ser Gly Leu Ser Glu Gly Thr Gly Ser Ser Asn Thr Pro Glu Glu
        515                 520                 525

Thr Asp Asp Val Asp Asn Ser Ser Leu Asp Ala Ser Ser Ser Met Ser
    530                 535                 540

Val Ala Pro Trp Ala Gly Ala Ala Thr Pro Leu Leu Pro Thr Glu Asn
545                 550                 555                 560

Gly Glu Gly Arg Leu Arg Val Ile Val Gly Arg Glu Ala Asp Ser Ser
                565                 570                 575

Ser Glu Ala Cys Val Gly Leu Glu Pro Pro Gln Asp Val Thr
            580                 585                 590
```

(2) INFORMATION FOR SEQ ID NO:3:

(i) SEQUENCE CHARACTERISTICS:
        (A) LENGTH: 3459 base pairs
        (B) TYPE: nucleic acid
        (C) STRANDEDNESS: double (D) TOPOLOGY: linear (ii) MOLECULE TYPE: DNA (genomic)

(ix) FEATURE:
        (A) NAME/KEY: CDS
        (B) LOCATION: 34..1908

(xi) SEQUENCE DESCRIPTION: SEQ ID NO:3:

```
GCAGGCGCGC CGGAGCCGGC CCCGTAGCGT GCC ATG GCC TGC TAC ATC TAC CAG      54
                                    Met Ala Cys Tyr Ile Tyr Gln
                                    1               5

CTG CCC TCC TGG GTG CTG GAC GAC CTG TGC CGC AAC ATG GAC GCG CTC      102
Leu Pro Ser Trp Val Leu Asp Asp Leu Cys Arg Asn Met Asp Ala Leu
            10                  15                  20

AGC GAG TGG GAC TGG ATG GAG TTC GCC TCC TAC GTG ATC ACA GAC CTG      150
Ser Glu Trp Asp Trp Met Glu Phe Ala Ser Tyr Val Ile Thr Asp Leu
        25                  30                  35

ACC CAG CTG CGG AAG ATC AAG TCC ATG GAG CGG GTG CAG GGT GTG AGC      198
Thr Gln Leu Arg Lys Ile Lys Ser Met Glu Arg Val Gln Gly Val Ser
40                  45                  50                  55

ATC ACG CGG GAG CTG CTG TGG TGG TGG GGC ATG CGG CAG GCC ACC GTC      246
Ile Thr Arg Glu Leu Leu Trp Trp Trp Gly Met Arg Gln Ala Thr Val
                60                  65                  70

CAG CAA CTT GTG GAC CTC CTG TGC CGC CTG GAG CTC TAC CGG GCT GCC      294
Gln Gln Leu Val Asp Leu Leu Cys Arg Leu Glu Leu Tyr Arg Ala Ala
            75                  80                  85

CAG ATC ATC CTG AAC TGG AAA CCG GCT CCT GAA ATC AGG TGT CCC ATT      342
Gln Ile Ile Leu Asn Trp Lys Pro Ala Pro Glu Ile Arg Cys Pro Ile
        90                  95                  100

CCA GCC TTC CCT GAC TCT GTG AAG CCA GAA AAG CCT TTG GCA GCT TCT      390
Pro Ala Phe Pro Asp Ser Val Lys Pro Glu Lys Pro Leu Ala Ala Ser
105                 110                 115

GTA AGA AAG GCT GAG GAT GAA CAG GAA GAG GGG CAG CCT GTG AGG ATG      438
Val Arg Lys Ala Glu Asp Glu Gln Glu Glu Gly Gln Pro Val Arg Met
120                 125                 130                 135

GCC ACC TTT CCA GGC CCA GGG TCC TCT CCA GCC AGA GCC CAC CAG CCG      486
Ala Thr Phe Pro Gly Pro Gly Ser Ser Pro Ala Arg Ala His Gln Pro
                140                 145                 150

GCC TTT CTC CAG CCT CCT GAA GAA GAT GCC CCT CAT TCC TTG AGA AGC      534
Ala Phe Leu Gln Pro Pro Glu Glu Asp Ala Pro His Ser Leu Arg Ser
            155                 160                 165

GAC CTC CCC ACT TCG TCT GAT TCA AAG GAC TTC AGC ACC TCC ATT CCT      582
Asp Leu Pro Thr Ser Ser Asp Ser Lys Asp Phe Ser Thr Ser Ile Pro
        170                 175                 180

AAG CAG GAA AAA CTT TTG AGC TTG GCT GGA GAC AGC CTT TTC TGG AGT      630
Lys Gln Glu Lys Leu Leu Ser Leu Ala Gly Asp Ser Leu Phe Trp Ser
185                 190                 195

GAG GCA GAC GTG GTC CAG GCA ACC GAT GAC TTC AAT CAA AAC CGC AAA      678
Glu Ala Asp Val Val Gln Ala Thr Asp Asp Phe Asn Gln Asn Arg Lys
200                 205                 210                 215

ATC AGC CAG GGG ACC TTT GCT GAC GTC TAC AGA GGG CAC AGG CAC GGG      726
Ile Ser Gln Gly Thr Phe Ala Asp Val Tyr Arg Gly His Arg His Gly
                220                 225                 230

AAG CCA TTC GTC TTC AAG AAG CTC AGA GAG ACA GCC TGT TCA AGT CCA      774
Lys Pro Phe Val Phe Lys Lys Leu Arg Glu Thr Ala Cys Ser Ser Pro
            235                 240                 245

GGA TCA ATC GAA AGA TTC TTC CAG GCA GAG TTG CAG ATT TGT CTT AGA      822
Gly Ser Ile Glu Arg Phe Phe Gln Ala Glu Leu Gln Ile Cys Leu Arg
        250                 255                 260

TGC TGC CAC CCC AAT GTC TTA CCT GTG CTG GGC TTC TGT GCT GCA AGA      870
```

```
Cys Cys His Pro Asn Val Leu Pro Val Leu Gly Phe Cys Ala Ala Arg
265                 270                 275

CAG TTT CAC AGC TTC ATC TAC CCC TAC ATG GCA AAT GGT TCC CTA CAG          918
Gln Phe His Ser Phe Ile Tyr Pro Tyr Met Ala Asn Gly Ser Leu Gln
280                 285                 290                 295

GAC AGA CTG CAG GGT CAG GGT GGC TCG GAC CCC CTC CCC TGG CCC CAG          966
Asp Arg Leu Gln Gly Gln Gly Gly Ser Asp Pro Leu Pro Trp Pro Gln
                300                 305                 310

CGT GTC AGC ATC TGC TCA GGG CTG CTC TGT GCC GTC GAG TAC CTG CAT         1014
Arg Val Ser Ile Cys Ser Gly Leu Leu Cys Ala Val Glu Tyr Leu His
            315                 320                 325

GGT CTG GAG ATC ATC CAC AGC AAC GTC AAG AGC TCT AAT GTC TTG CTG         1062
Gly Leu Glu Ile Ile His Ser Asn Val Lys Ser Ser Asn Val Leu Leu
        330                 335                 340

GAC CAA AAT CTC ACC CCC AAA CTT GCT CAC CCA ATG GCT CAT CTG TGT         1110
Asp Gln Asn Leu Thr Pro Lys Leu Ala His Pro Met Ala His Leu Cys
    345                 350                 355

CCT GTC AAC AAA AGG TCA AAA TAC ACC ATG ATG AAG ACT CAC CTG CTC         1158
Pro Val Asn Lys Arg Ser Lys Tyr Thr Met Met Lys Thr His Leu Leu
360                 365                 370                 375

CGG ACG TCA GCC GCG TAT CTG CCA GAG GAT TTC ATC CGG GTG GGG CAG         1206
Arg Thr Ser Ala Ala Tyr Leu Pro Glu Asp Phe Ile Arg Val Gly Gln
                380                 385                 390

GTG ACA AAG CGA GTG GAC ATC TTC AGC TGT GGA ATA GTG TTG GCC GAG         1254
Val Thr Lys Arg Val Asp Ile Phe Ser Cys Gly Ile Val Leu Ala Glu
            395                 400                 405

GTC CTC ACG GGC ATC CCT GCA ATG GAT AAC AAC CGA AGC CCG GTT TAC         1302
Val Leu Thr Gly Ile Pro Ala Met Asp Asn Asn Arg Ser Pro Val Tyr
        410                 415                 420

CTG AAG GAC TTA CTC CTC AGT GAA ATT CCA AGC AGC ACC GCC TCG CTC         1350
Leu Lys Asp Leu Leu Leu Ser Glu Ile Pro Ser Ser Thr Ala Ser Leu
    425                 430                 435

TGC TCC AGG AAG ACG GGC GTG GAG AAC GTG ATG GCA AAG GAG ATC TGC         1398
Cys Ser Arg Lys Thr Gly Val Glu Asn Val Met Ala Lys Glu Ile Cys
440                 445                 450                 455

CAG AAG TAC CTG GAG AAG GGC GCA GGG AGG CTT CCG GAG GAC TGC GCC         1446
Gln Lys Tyr Leu Glu Lys Gly Ala Gly Arg Leu Pro Glu Asp Cys Ala
                460                 465                 470

GAG GCC CTG GCC ACG GCT GCC TGC CTG TGC CTG CGG AGG CGT AAC ACC         1494
Glu Ala Leu Ala Thr Ala Ala Cys Leu Cys Leu Arg Arg Arg Asn Thr
            475                 480                 485

AGC CTG CAG GAG GTG TGT GGC TCT GTG GCT GCT GTG GAA GAG CGG CTC         1542
Ser Leu Gln Glu Val Cys Gly Ser Val Ala Ala Val Glu Glu Arg Leu
        490                 495                 500

CGA GGT CGG GAG ACG TTG CTC CCT TGG AGT GGG CTT TCT GAG GGT ACA         1590
Arg Gly Arg Glu Thr Leu Leu Pro Trp Ser Gly Leu Ser Glu Gly Thr
    505                 510                 515

GGC TCT TCT TCC AAC ACC CCA GAG GAA ACA GAC GAC GTT GAC AAT TCC         1638
Gly Ser Ser Ser Asn Thr Pro Glu Glu Thr Asp Asp Val Asp Asn Ser
520                 525                 530                 535

AGC CTT GAT GCC TCC TCC TCC ATG AGT GTG GCA CCC TGG GCA GGG GCT         1686
Ser Leu Asp Ala Ser Ser Ser Met Ser Val Ala Pro Trp Ala Gly Ala
                540                 545                 550

GCC ACC CCA CTT CTC CCC ACA GAG AAT GGG GAA GGA AGG CTG CGG GTC         1734
Ala Thr Pro Leu Leu Pro Thr Glu Asn Gly Glu Gly Arg Leu Arg Val
            555                 560                 565

ATC GTG GGA AGG GAG GCT GAC TCC TCC TCT GAG GCC TGT GTT GGC CTG         1782
Ile Val Gly Arg Glu Ala Asp Ser Ser Ser Glu Ala Cys Val Gly Leu
        570                 575                 580
```

-continued

```
GAG CCT CCC CAG GAT GTT ACA GAA ACT TCG TGG CAA ATT GAG ATC AAT    1830
Glu Pro Pro Gln Asp Val Thr Glu Thr Ser Trp Gln Ile Glu Ile Asn
        585                 590                 595

GAG GCC AAA AGG AAA CTG ATG GAG AAT ATT CTG CTC TAC AAA GAG GAA    1878
Glu Ala Lys Arg Lys Leu Met Glu Asn Ile Leu Leu Tyr Lys Glu Glu
610             605                 610                 615

AAA GTG GAC AGC ATT GAG CTC TTT GGC CCC TGATGACCGG AACACAGCTG      1928
Lys Val Asp Ser Ile Glu Leu Phe Gly Pro
                620             625

AGGACCCTTG TCCTCAGTTG GAAAGATGAG CATCAGATCA AGAAAAAGGT CTGAGGCAGA  1988
ATCCAAGATC TGCCAGGAAA CACACAACAA AACATCTGCT GTCCTGGGTG GGAGGGAAAC  2048
TTCATTTCAC TGGAATGAGT TGGGAGAGAA AGGCCCTCAG CTTTTAGAGA CACAAAAATC  2108
CATGAAGTCT CTTCCTTTCT GGGCTTTGTT AGTCAGAGCA GGGGATCAGA GGAGACTGAA  2168
GCAGAAACCC TGCACACGGG CCCAGGATGT GGCTGATTTT GTGGTTCCGG GGAGTATGTG  2228
ATGATAATCA CCCCCAGCAG ATTCCATTAC CTCAGCAGCT CTTGTTCCCC CGCCACTGGC  2288
AGTTCTGCAA TGCCATAGCA TTTTCCAGAG CTAAGATCTC TGGGTTGTAT TTGCTGACAG  2348
CCTGCAAGCT TGCATGCTCT GAAAGATTTT TTTAGTTTTT AATTTTTTTG TAAAAATGGG  2408
GTCTCGCTTT GTTGGCGCAA TCCTCCCACC TCAGACTCCC AAAGTGCTGG AATTACATTG  2468
GGAACCACTG TGCCTGGCCT GGAAAACTTC CAACTTGTGT TCTCAGTGCA GTTCTGACTC  2528
ACCTCTCTGG GCCTCAGGTT CTACAAATGC CAGACACCTA GCGAAGAGCT CTGCAGGCTT  2588
TCCACTGCCT GTATTGGAAA TCTTGCAATT CACATAATTA TTCAGTCACT GCCTGGTACC  2648
TTTATCTTCC CATCCCATTA ATGTTAGTGT TTTTTAATGG AGCTTTTATT CTGAGAATAT  2708
GTGTTCGTCT GTTTGTTTGT TTTTTGAGAC AGAGTCTCAC TTTGTCACCC AGGCTGGAGT  2768
GCAGTGGCAC GATCTCAGCT CACTGCAAGC TGTGCCTCTC AGGTTTCAAG TGATTCTCCT  2828
GCCTCAGCCT CCTGAGTAGA TGGGACTGTA GGCACCTGCC ACTATGCCTG GCTAATTTTT  2888
GTGTTTTTAG TAGAGACAGG GTTTCACCAT ATTGGCCAGG CTGGTCTCGA ACTACTGACC  2948
TCGTGATCTG CCCGCCTTGG CCTATCAAAG TGTTGGGATT ACAGGCTTGA GCCACCGCAC  3008
CCGGCCGAGA ATATGTGTTG TTATTTATGA CTGGATTATG AAGAATCAGG AGAATGCATT  3068
TCATGTCTGA TTCTGCTGCT AATTAAGTCA ATCATTTAAT TTTTGGGACC TCAGTTTCTT  3128
TGTAAGTAAA ATAACACCTG CTTGTTCTTC ATCCCTGGGC TGTTGGGAGG AACAGATGAG  3188
ACAGTGGCTA TAGAAGCACT TGGAAAATGC ACTTGTCCTG TTTTGTAAAA TAAAAGGTA   3248
TTAAATGTGT ATTTCTGCCA TGTACCTAAT GATTATTCAG TGCGTATATA TCTGAAAAGT  3308
CATGTTGCAA ATCTTTCTGT GAAACAGATG CTATTTTAAA TTCACTGGGA GAAATATCCT  3368
ATTTAAAGTA ATCTATAGTA ATTTCTTTTT ATATAATAAA AATATATTTG TAAAGTCGAA  3428
AAAAAAAAAA AAAAAAAAA AAAAAAAAA A                                  3459
```

(2) INFORMATION FOR SEQ ID NO:4:

(i) SEQUENCE CHARACTERISTICS:
        (A) LENGTH: 625 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Cys Tyr Ile Tyr Gln Leu Pro Ser Trp Val Leu Asp Asp Leu
 1               5                  10                  15
```

-continued

```
Cys Arg Asn Met Asp Ala Leu Ser Glu Trp Asp Trp Met Glu Phe Ala
             20                  25                  30

Ser Tyr Val Ile Thr Asp Leu Thr Gln Leu Arg Lys Ile Lys Ser Met
         35                  40                  45

Glu Arg Val Gln Gly Val Ser Ile Thr Arg Glu Leu Leu Trp Trp Trp
     50                  55                  60

Gly Met Arg Gln Ala Thr Val Gln Gln Leu Val Asp Leu Leu Cys Arg
 65                  70                  75                  80

Leu Glu Leu Tyr Arg Ala Ala Gln Ile Ile Leu Asn Trp Lys Pro Ala
                 85                  90                  95

Pro Glu Ile Arg Cys Pro Ile Pro Ala Phe Pro Asp Ser Val Lys Pro
            100                 105                 110

Glu Lys Pro Leu Ala Ala Ser Val Arg Lys Ala Glu Asp Glu Gln Glu
        115                 120                 125

Glu Gly Gln Pro Val Arg Met Ala Thr Phe Pro Gly Pro Gly Ser Ser
    130                 135                 140

Pro Ala Arg Ala His Gln Pro Ala Phe Leu Gln Pro Pro Glu Glu Asp
145                 150                 155                 160

Ala Pro His Ser Leu Arg Ser Asp Leu Pro Thr Ser Ser Asp Ser Lys
                165                 170                 175

Asp Phe Ser Thr Ser Ile Pro Lys Gln Glu Lys Leu Leu Ser Leu Ala
            180                 185                 190

Gly Asp Ser Leu Phe Trp Ser Glu Ala Asp Val Val Gln Ala Thr Asp
        195                 200                 205

Asp Phe Asn Gln Asn Arg Lys Ile Ser Gln Gly Thr Phe Ala Asp Val
    210                 215                 220

Tyr Arg Gly His Arg His Gly Lys Pro Phe Val Phe Lys Lys Leu Arg
225                 230                 235                 240

Glu Thr Ala Cys Ser Ser Pro Gly Ser Ile Glu Arg Phe Phe Gln Ala
                245                 250                 255

Glu Leu Gln Ile Cys Leu Arg Cys His Pro Asn Val Leu Pro Val
            260                 265                 270

Leu Gly Phe Cys Ala Ala Arg Gln Phe His Ser Phe Ile Tyr Pro Tyr
        275                 280                 285

Met Ala Asn Gly Ser Leu Gln Asp Arg Leu Gln Gly Gln Gly Gly Ser
    290                 295                 300

Asp Pro Leu Pro Trp Pro Gln Arg Val Ser Ile Cys Ser Gly Leu Leu
305                 310                 315                 320

Cys Ala Val Glu Tyr Leu His Gly Leu Glu Ile Ile His Ser Asn Val
                325                 330                 335

Lys Ser Ser Asn Val Leu Leu Asp Gln Asn Leu Thr Pro Lys Leu Ala
            340                 345                 350

His Pro Met Ala His Leu Cys Pro Val Asn Lys Arg Ser Lys Tyr Thr
        355                 360                 365

Met Met Lys Thr His Leu Leu Arg Thr Ser Ala Ala Tyr Leu Pro Glu
    370                 375                 380

Asp Phe Ile Arg Val Gly Gln Val Thr Lys Arg Val Asp Ile Phe Ser
385                 390                 395                 400

Cys Gly Ile Val Leu Ala Glu Val Leu Thr Gly Ile Pro Ala Met Asp
                405                 410                 415

Asn Asn Arg Ser Pro Val Tyr Leu Lys Asp Leu Leu Leu Ser Glu Ile
            420                 425                 430

Pro Ser Ser Thr Ala Ser Leu Cys Ser Arg Lys Thr Gly Val Glu Asn
```

-continued

```
                435                 440                 445
Val Met Ala Lys Glu Ile Cys Gln Lys Tyr Leu Glu Lys Gly Ala Gly
    450                 455                 460

Arg Leu Pro Glu Asp Cys Ala Glu Ala Leu Ala Thr Ala Ala Cys Leu
465                 470                 475                 480

Cys Leu Arg Arg Arg Asn Thr Ser Leu Gln Glu Val Cys Gly Ser Val
                485                 490                 495

Ala Ala Val Glu Glu Arg Leu Arg Gly Arg Glu Thr Leu Leu Pro Trp
            500                 505                 510

Ser Gly Leu Ser Glu Gly Thr Gly Ser Ser Ser Asn Thr Pro Glu Glu
        515                 520                 525

Thr Asp Asp Val Asp Asn Ser Ser Leu Asp Ala Ser Ser Ser Met Ser
    530                 535                 540

Val Ala Pro Trp Ala Gly Ala Thr Pro Leu Leu Pro Thr Glu Asn
545                 550                 555                 560

Gly Glu Gly Arg Leu Arg Val Ile Val Gly Arg Glu Ala Asp Ser Ser
                565                 570                 575

Ser Glu Ala Cys Val Gly Leu Glu Pro Pro Gln Asp Val Thr Glu Thr
            580                 585                 590

Ser Trp Gln Ile Glu Ile Asn Glu Ala Lys Arg Lys Leu Met Glu Asn
        595                 600                 605

Ile Leu Leu Tyr Lys Glu Glu Lys Val Asp Ser Ile Glu Leu Phe Gly
    610                 615                 620

Pro
625

(2) INFORMATION FOR SEQ ID NO:5:

(i) SEQUENCE CHARACTERISTICS:
        (A) LENGTH: 712 amino acids
        (B) TYPE: amino acid
        (C) STRANDEDNESS: single
        (D) TOPOLOGY: Not Relevant (ii) MOLECULE TYPE: protein (xi) SEQUENCE DESCRIPTION: SEQ ID NO:5:

Met Ala Gly Gly Pro Gly Pro Gly Glu Pro Ala Ala Pro Gly Ala Gln
1               5                   10                  15

His Phe Leu Tyr Glu Val Pro Pro Trp Val Met Cys Arg Phe Tyr Lys
            20                  25                  30

Val Met Asp Ala Leu Glu Pro Ala Asp Trp Cys Gln Phe Ala Ala Leu
        35                  40                  45

Ile Val Arg Asp Gln Thr Glu Leu Arg Leu Cys Glu Arg Ser Gly Gln
    50                  55                  60

Arg Thr Ala Ser Val Leu Trp Pro Trp Ile Asn Arg Asn Ala Arg Val
65                  70                  75                  80

Ala Asp Leu Val His Ile Leu Thr His Leu Gln Leu Leu Arg Ala Arg
                85                  90                  95

Asp Ile Ile Thr Ala Trp His Pro Ala Pro Leu Pro Ser Pro Gly
            100                 105                 110

Thr Thr Ala Pro Arg Pro Ser Ser Ile Pro Ala Pro Ala Glu Ala Glu
        115                 120                 125

Ala Trp Ser Pro Arg Lys Leu Pro Ser Ala Ser Thr Phe Leu Ser
    130                 135                 140

Pro Ala Phe Pro Gly Ser Gln Thr His Ser Gly Pro Glu Leu Gly Leu
```

-continued

```
145                 150                 155                 160
Val Pro Ser Pro Ala Ser Leu Trp Pro Pro Pro Ser Pro Ala Pro
                165                 170                 175
Ser Ser Thr Lys Pro Gly Pro Glu Ser Ser Val Ser Leu Leu Gln Gly
            180                 185                 190
Ala Arg Pro Ser Pro Phe Cys Trp Pro Leu Cys Glu Ile Ser Arg Gly
        195                 200                 205
Thr His Asn Phe Ser Glu Glu Leu Lys Ile Gly Glu Gly Gly Phe Gly
    210                 215                 220
Cys Val Tyr Arg Ala Val Met Arg Asn Thr Val Tyr Ala Val Lys Arg
225                 230                 235                 240
Leu Lys Glu Asn Ala Asp Leu Glu Trp Thr Ala Val Lys Gln Ser Phe
                245                 250                 255
Leu Thr Glu Val Glu Gln Leu Ser Arg Phe Arg His Pro Asn Ile Val
            260                 265                 270
Asp Phe Ala Gly Tyr Cys Ala Gln Asn Gly Phe Tyr Cys Leu Val Tyr
        275                 280                 285
Gly Phe Leu Pro Asn Gly Ser Leu Glu Asp Arg Leu His Cys Gln Thr
    290                 295                 300
Gln Ala Cys Pro Pro Leu Ser Trp Pro Gln Arg Leu Asp Ile Leu Leu
305                 310                 315                 320
Gly Thr Ala Arg Ala Ile Gln Phe Leu His Gln Asp Ser Pro Ser Leu
                325                 330                 335
Ile His Gly Asp Ile Lys Ser Ser Asn Val Leu Leu Asp Glu Arg Leu
            340                 345                 350
Thr Pro Lys Leu Gly Asp Phe Gly Leu Ala Arg Phe Ser Arg Phe Ala
        355                 360                 365
Gly Ser Ser Pro Ser Gln Ser Ser Met Val Ala Arg Thr Gln Thr Val
    370                 375                 380
Arg Gly Thr Leu Ala Tyr Leu Pro Glu Glu Tyr Ile Lys Thr Gly Arg
385                 390                 395                 400
Leu Ala Val Asp Thr Asp Thr Phe Ser Phe Gly Val Val Val Leu Glu
                405                 410                 415
Thr Leu Ala Gly Gln Arg Ala Val Lys Thr His Gly Ala Arg Thr Lys
            420                 425                 430
Tyr Leu Lys Asp Leu Val Glu Glu Ala Glu Ala Gly Val Ala
        435                 440                 445
Leu Arg Ser Thr Gln Ser Thr Leu Gln Ala Gly Leu Ala Ala Asp Ala
    450                 455                 460
Trp Ala Ala Pro Ile Ala Met Gln Ile Tyr Lys Lys His Leu Asp Pro
465                 470                 475                 480
Arg Pro Gly Pro Cys Pro Pro Glu Leu Gly Leu Gly Leu Gly Gln Leu
                485                 490                 495
Ala Cys Cys Cys Leu His Arg Arg Ala Lys Arg Arg Pro Pro Met Thr
            500                 505                 510
Gln Val Tyr Glu Arg Leu Glu Lys Leu Gln Ala Val Val Ala Gly Val
        515                 520                 525
Pro Gly His Leu Glu Ala Ala Ser Cys Ile Pro Pro Ser Pro Gln Glu
    530                 535                 540
Asn Ser Tyr Val Ser Ser Thr Gly Arg Ala His Ser Gly Ala Ala Pro
545                 550                 555                 560
Trp Gln Pro Leu Ala Ala Pro Ser Gly Ala Ser Ala Gln Ala Ala Glu
                565                 570                 575
```

```
Gln Leu Gln Arg Gly Pro Asn Gln Pro Val Glu Ser Asp Glu Ser Leu
            580                 585                 590

Gly Gly Leu Ser Ala Ala Leu Arg Ser Trp His Leu Thr Pro Ser Cys
        595                 600                 605

Pro Leu Asp Pro Ala Pro Leu Arg Glu Ala Gly Cys Pro Gln Gly Asp
        610                 615                 620

Thr Ala Gly Glu Ser Ser Trp Gly Ser Gly Pro Gly Ser Arg Pro Thr
625                 630                 635                 640

Ala Val Glu Gly Leu Ala Leu Gly Ser Ser Ala Ser Ser Ser Ser Glu
                645                 650                 655

Pro Pro Gln Ile Ile Ile Asn Pro Ala Arg Gln Lys Met Val Gln Lys
            660                 665                 670

Leu Ala Leu Tyr Glu Asp Gly Ala Leu Asp Ser Leu Gln Leu Leu Ser
            675                 680                 685

Ser Ser Ser Leu Pro Gly Leu Gly Leu Glu Gln Asp Arg Gln Gly Pro
        690                 695                 700

Glu Glu Ser Asp Glu Phe Gln Ser
705                 710
```

(2) INFORMATION FOR SEQ ID NO:6:

(i) SEQUENCE CHARACTERISTICS:
        (A) LENGTH: 501 amino acids
        (B) TYPE: amino acid
        (C) STRANDEDNESS: single
        (D) TOPOLOGY: Not Relevant (ii) MOLECULE TYPE: protein (xi) SEQUENCE DESCRIPTION: SEQ ID NO:6:

```
Met Ser Gly Val Gln Thr Ala Glu Ala Glu Ala Gln Ala Gln Asn Gln
1               5                   10                  15

Ala Asn Gly Asn Arg Thr Arg Ser Arg Ser His Leu Asp Asn Thr Met
                20                  25                  30

Ala Ile Arg Leu Leu Pro Leu Pro Val Arg Ala Gln Leu Cys Ala His
            35                  40                  45

Leu Asp Ala Leu Asp Val Trp Gln Gln Leu Ala Thr Ala Val Lys Leu
50                  55                  60

Tyr Pro Asp Gln Val Glu Gln Ile Ser Ser Gln Lys Gln Arg Gly Arg
65                  70                  75                  80

Ser Ala Ser Asn Glu Phe Leu Asn Ile Trp Gly Gly Gln Tyr Asn His
                85                  90                  95

Thr Val Gln Thr Leu Phe Ala Leu Phe Lys Lys Leu Lys Leu His Asn
            100                 105                 110

Ala Met Arg Leu Ile Lys Asp Tyr Val Ser Glu Asp Leu His Lys Tyr
        115                 120                 125

Ile Pro Arg Ser Val Pro Thr Ile Ser Glu Leu Arg Ala Ala Pro Asp
        130                 135                 140

Ser Ser Ala Lys Val Asn Asn Gly Pro Pro Phe Pro Ser Ser Ser Gly
145                 150                 155                 160

Val Ser Asn Ser Asn Asn Asn Arg Thr Ser Thr Thr Ala Thr Glu Glu
                165                 170                 175

Ile Pro Ser Leu Glu Ser Leu Gly Asn Ile His Ile Ser Thr Val Gln
            180                 185                 190

Arg Ala Ala Glu Ser Leu Leu Glu Ile Asp Tyr Ala Glu Leu Glu Asn
        195                 200                 205
```

```
Ala Thr Asp Gly Trp Ser Pro Asp Asn Arg Leu Gly Gln Gly Gly Phe
    210                 215                 220
Gly Asp Val Tyr Arg Gly Lys Trp Lys Gln Leu Asp Val Ala Ile Lys
225                 230                 235                 240
Val Met Asn Tyr Arg Ser Pro Asn Ile Asp Gln Lys Met Val Glu Leu
                245                 250                 255
Gln Gln Ser Tyr Asn Glu Leu Lys Tyr Leu Asn Ser Ile Arg His Asp
                260                 265                 270
Asn Ile Leu Ala Leu Tyr Gly Tyr Ser Ile Lys Gly Gly Lys Pro Cys
            275                 280                 285
Leu Val Tyr Gln Leu Met Lys Gly Gly Ser Leu Glu Ala Arg Leu Arg
    290                 295                 300
Ala His Lys Ala Gln Asn Pro Leu Pro Ala Leu Thr Trp Gln Gln Arg
305                 310                 315                 320
Phe Ser Ile Ser Leu Gly Thr Ala Arg Gly Ile Tyr Phe Leu His Thr
                325                 330                 335
Ala Arg Gly Thr Pro Leu Ile His Gly Asp Ile Lys Pro Ala Asn Ile
                340                 345                 350
Leu Leu Asp Gln Cys Leu Gln Pro Lys Ile Gly Asp Phe Gly Leu Val
            355                 360                 365
Arg Glu Gly Pro Lys Ser Leu Asp Ala Val Val Glu Val Asn Lys Val
    370                 375                 380
Phe Gly Thr Lys Ile Tyr Leu Pro Pro Glu Phe Arg Asn Phe Arg Gln
385                 390                 395                 400
Leu Ser Thr Gly Val Asp Val Tyr Ser Phe Gly Ile Val Leu Leu Glu
                405                 410                 415
Val Phe Thr Gly Arg Gln Val Thr Asp Arg Val Pro Glu Asn Glu Thr
                420                 425                 430
Lys Lys Asn Leu Leu Asp Tyr Val Lys Gln Gln Trp Arg Gln Asn Arg
            435                 440                 445
Met Glu Leu Leu Glu Lys His Leu Ala Ala Pro Met Gly Lys Glu Leu
    450                 455                 460
Asp Met Cys Met Cys Ala Ile Glu Ala Gly Leu His Cys Thr Ala Leu
465                 470                 475                 480
Asp Pro Gln Asp Arg Pro Ser Met Asn Ala Val Leu Lys Arg Phe Glu
                485                 490                 495
Pro Phe Val Thr Asp
            500

(2) INFORMATION FOR SEQ ID NO:7:

(i) SEQUENCE CHARACTERISTICS:
        (A) LENGTH: 265 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:7:

GGCACGAGCA CCTTTCCAGG CCCAGGGTCC TNTCCAGCCA GAGCCCACCA GCCGGCCTTT        60

CTCCAGCCTC CTGAAGAAGA TNNCCCTCAT TCCTTGAGAA GCGACCTCCC CACTTCGTCT       120

GNTTCAAAGG ACTTCAGCAC CTCCATTCCT AAGCAGGAAA AACTTTTGAG CTTGGCTGGA       180

GACAGATGNT TCTGGTGTGA GGCAGACGTG GTCCAGTCAA CCGATGACTT GANTNNTAAC       240
```

```
CGCAGAATCA GNCAGGGGAC CTTTG                                         265

(2) INFORMATION FOR SEQ ID NO:8:

(i) SEQUENCE CHARACTERISTICS:
        (A) LENGTH: 294 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:8:

AACGTCAAGA GCTCTAATNT CTTGCTGGAC CAAAATCTNA CCCCCAAACT TGCTCACCCA    60

ATGGCTCATC TGTGTCCTGT NAACAAAAGG TCAAAATACA CCATGATGAT GACTCACCTG   120

GCTCCGGAAC GTCAGCCGCG TATCTCCCAG NGGATTTNAT CCGGAGTGGG GCAGCTGAAC   180

AAAGCGAGTG GACATCTTCA GCTGTGGAAT AGTGTTGGAC GAGGTNCTCA CGGGGNATCC   240

CTGTCAATGG GTTAACANCC GAAGCCCGGT TTACCTGAAG GNACTTAATT NCTC         294

(2) INFORMATION FOR SEQ ID NO:9:

(i) SEQUENCE CHARACTERISTICS:
        (A) LENGTH: 330 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:9:

CNCTAATGTN TTNCTGGACC AAAATNTCAC CCCCAAACTT CCTCACCCAA TGGCTCATCT    60

NTTTCCTGTC AACAAAAGGT CAAAATACAC CATGATGAAG ACTCACCTGC TCCGGACGTC   120

AGCCGCGTAT CTGCCCAGAG GATTTCATCC GNGTGGGGCA GCTGACAAAG CGAGTGGACA   180

TCTTCAGCTG TGGAATAGTA AGAGTGTCCT GCTCTGCGTA GAAGTGGGGC CCACCTTGAA   240

TTTGTCCTTC CCACGGTTCC TTTGTNAATC ACAGGATACG GTAGAGNCAC ACAGACAGGT   300

TCCNNCAAGT NACAACAGGG GCTGTACAAA                                   330

(2) INFORMATION FOR SEQ ID NO:10:

(i) SEQUENCE CHARACTERISTICS:
        (A) LENGTH: 499 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:10:

AATTCGGCAN AGNATGGAGT TCGCCTCCTA CGTGATCACA GACCTGACCC AGCTGCGGAA    60

GATCAAGTCC ATGGAGCGGG TGCAGGGTGT GAGCATCACG CGGGGNGCTG CTGTGGTGGT   120

GGGGCATGCG GCAGGCCACC GTCCAGCAAC TTGTGGGACC TCCTGTGCCG CCTGGGAGCT   180

CTACCGGGNT GCCCAGATCA TCCTGGAACT TGTGGACACA AGACTTCTCA CATCTGAGAT   240

GGCCCCTCTG TGCCCCTACA TGCACATTGG CAGACAGCAA GAAGGGAAAA AGAGGGAAAA   300

AGGGAAACCG GCTNCTGGAA ATCAGGTGTN CCCATTTCCA GNCTTTCCCT GAATTCTNTG   360

GAAGGCCAGA AAAAGCCTTT TGGCAAGGTT TTTGTTAAGN AAAGGNTNNA GGTTGAACCA   420

GGAAGAGGGG GCAGNCTTTN AAGGNNTGGG CCACTTTTTN CAGGGCCCCA GGGGTCCTTT   480
```

TNCAGCCCGN GGNCCAACC                                                499

(2) INFORMATION FOR SEQ ID NO:11:

(i) SEQUENCE CHARACTERISTICS:
        (A) LENGTH: 413 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:11:

GGGCACNAGG NGGGTCATCG TGGGAAGGGA AGGCTGACTC CTCCTCTGAA GGACTGTTTT      60

GGANCTAGAG CGTCCCCAGG NTGTTACAGA AACTTCGTGG NNAAATTGAG AATCAATGAG     120

GGCAAAAGGA AACTGATGGN GAATATTCTG CTCTACAANG AGGGAGAAAG TGGNCAGNAT     180

TGAGCTNTTT GGCCCCTAAT GACCGGAACA GAGCTGAGGN NCCTTGTCCT CAGTTGGAAA     240

GATGAGCATC AGATCAAGAA AAAGGTCTGA GGTAGANTNC AAGATCTGNC ANGNAACANA     300

CANCANGACA TCTGCTGTCC TNGGTGGGGG GGAAACTTAT TTACTGGAAT GAGTTTGGAG     360

AGAAAGGCCC TCAANATTTT GGTGGCACAA ANATCCATGA AGGNTATTCG ATN           413

(2) INFORMATION FOR SEQ ID NO:12:

(i) SEQUENCE CHARACTERISTICS:
        (A) LENGTH: 665 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:12:

AGAGAAGCCG CAGCCCGCAG TGTCCGACCC AGTCGTCCCG CGCCGGAGCC GGCCCCGTAG      60

CGTGCCATGG CCTGCTACAT CTACCAGCTG CCCTCCTGGG TGCTGGACGA CCTGTGCCGC     120

AACATGGACG CGCTCAGGAG TGGGACTGGA TGGAGTTCGG TGAGTGCGGC CCGGGGAGGG     180

GAGGGGACCA GGGCGACCGG AGCCCCCAGC GATCCCGCCT GGAGCGGCCG CCAAGCTCCC     240

TCGGGCACCC GGGTTCAGCG GGTCCCGATC CGAGGGCGTG CGAGCTGAGC CTTCCTGGAC     300

CGGGTTCCGC CGCGGACCTT CGGCCTGTTC ACCTGAAGGT GCCGGTGGTC TCTGAGGACG     360

TCTGTTCGAC GAGCCAGGGG CCGCCGCCAC TGCGCTCTGA GTCCAGAGAA CGGTGGGTAC     420

GGGGGCCCTC CTGTCAGCGC TGCTGGCTCG GTGACGTCCC CAGGTGGCCT CTCATCCAGC     480

CCACAACAGC CTGCAAAGTG CGAGCCTCGA CCCTGTAGGG ACCCACGGTG CTGTCACTTC     540

TTGGGGGTGT GTGTGTGTGT GTGTGTGTGG TGTGTTTAGT TTTAGTGTAT ATTAGAAGGA     600

TCTATGATTT AACATATATA TATATATTGA AACAGAGCAA GATTCTGTCT CAAAAAAAAA     660

AAAAA                                                                665

(2) INFORMATION FOR SEQ ID NO:13:

(i) SEQUENCE CHARACTERISTICS:
        (A) LENGTH: 327 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:13:

-continued

```
AGGGAAACTG ATGGNGAATA TTCTGCTCTA CAAAGAGGNA AAAAGTGGAC AGCATTGAGC      60

TCTTTGGCCC CTGATGACCG GAACACAGCT GAGGACCCTT GTCCTCAGTT GGAAAGATGA     120

GCATCAGATC AAGAAAAAGG TCTGAGGCAG AATCCAAGAT CTGCCAGGAA ACACACAACA     180

AAACATCTGC TGTCCTGGGT GGGAGGGAAA CTTCATTTCA CTGGAATGAG TTGGGAGAGA     240

AAGGCCCTCA GCTTTTNGGG ANACAAAATT CCNTGAGGTT TTTCCCTTCN TGGTTTNTAA     300

GTAAGGGCAG GGTTAAGGGG TTTAGGA                                         327

(2) INFORMATION FOR SEQ ID NO:14:

(i) SEQUENCE CHARACTERISTICS:
        (A) LENGTH: 479 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:14:

AGTATTAAGG CCAGAGAGTG CAACTCACAC GGATGGAAAC TGCTCAGGAG CGTGATGGGC      60

CCCACCCAAG GAGGGCCTGG AGTTACTCAC AGTTCAGGAT GATCTGGGCA GCCCGGTAGA     120

GCTCCAGGCG GCACAGGAGG TCCACAAGTT GCTGGACGGT GGCCTGCCGC ATGCCCCACC     180

ACCACAGCAG CTCCCGCGTG ATGCTCACAC CCTGCACCCG CTCCATGGAC TTGATCTTCC     240

GCAGCTGGGT CAGGTCTGTG ATCACGTAGG AGGCTGGAAG GGACAGAGAG AACTCTGCTT     300

AGAGTCAGAG AGGCAGTCCC TCTAGGACAG GTCCCCACAC TAAGCCCCTA GCTTGGGTTT     360

TTCCAGGACA TCCTCCCCAA CCAACCGCCT CCACACTGGA AACACCACCA TTAAGCTGAG     420

GTCCACAGGT GGCCAAGTTA CAACGCTGAC TCTGCTGGGC ACCCATGGGG TCCAGTACA     479
```

HUMAN IRAK-2 ANTIBODIES

The present application is a divisional of U.S. patent application Ser. No. 08/980,060, filed Nov. 26, 1997 now U.S. Pat. No. 5,965,421, which is herein incorporated by reference.

FIELD OF THE INVENTION

The present invention relates to a novel interleukin-1 receptor signaling protein. More specifically, isolated nucleic acid molecules are provided encoding a human interleukin-1 receptor associated kinase-2 (IRAK-2). IRAK-2 polypeptides are also provided, as are vectors, host cells and recombinant methods for producing the same.

BACKGROUND OF THE INVENTION

Interleukin-1 (IL-1). Interleukin-1 (IL-1α and IL-1β) is a "multifunctional" cytokine that affects nearly every cell type, and often in concert with other cytokines or small mediator molecules. (Dinarello, C. A., *Blood* 87:2095–2147 (Mar. 15, 1996).) There are three members of the IL-1 gene family: IL-1α, IL-1β, and IL-1 receptor antagonist (IL-1Ra). IL-1α and IL-1β are agonists and IL-1Ra is a specific receptor antagonist. IL-1α and β are synthesized as precursors without leader sequences. The molecular weight of each precursor is 31 kD. Processing of IL-1α or IL-1β to "mature" forms of 17 kD requires specific cellular proteases. In contrast, IL-1Ra evolved with a signal peptide and is readily transported out of the cells and termed secreted IL-1Ra (sIL-1Ra).

IL-1 Receptor and Ligands. The receptors and ligands of the IL-1 pathway have been well defined (for review, see Dinarello, C. A., *FASEB J.* 8:1314–1325 (1994); Sims, J. E. et al., *Interleukin-1 signal transduction: Advances in Cell and Molecular Biology of Membranes and Organelles*, Vol.3, JAI Press, Inc., Greenwich, Conn. (1994), pp. 197–222). Three ligands, IL-1α, IL-1β, and IL-1 receptor antagonist (IL-1Ra) bind three forms of IL-1 receptor, an 80-kDa type I IL-1 receptor (IL-1R1) (Sims, J. E. et al., *Science* 241:585–589 (1988)), a 68-kDa type II IL-1 receptor (IL-1RII) (McMahan, C. J. et al., *EMBO J.* 10:2821–2832 (1991)), and a soluble form of the type II IL-1R (sIL-1RII) (Colotta, F. et al., *Science* 261:472–475 (1993)).

IL-1 production in various disease states. Increased IL-1 production has been reported in patients with various viral, bacterial, fungal, and parasitic infections; intravascular coagulation; high-dose IL-2 therapy; solid tumors; leukemias; Alzheimer's disease; HIV1 infection; autoimmune disorders; trauma (surgery); hemodialysis; ischemic diseases (myocardial infarction); noninfectious hepatitis; asthma; UV radiation; closed head injury; pancreatitis; periodontitis; graft-versus-host disease; transplant rejection; and in healthy subjects after strenuous exercise. There is an association of increased IL-1β production in patients with Alzheimer's disease and a possible role for IL-1 in the release of the amyloid precursor protein (Vasilakos, J. P., et al, *FEBS Lett.* 354:289 (1994)). However, in most conditions, IL-1 is not the only cytokine exhibiting increased production and hence the specificity of the IL-1 findings as related to the pathogenesis of any particular disease is lacking. In various disease states, IL-1β, but not IL-1α, is detected in the circulation.

IL-1 in Therapy. Although IL-1 has been found to exhibit many important biological activities, it is also found to be toxic at doses that are close to therapeutic dosages (Dinarello, C. A., *Blood* 87:2095–2147 (Mar. 15, 1996)). In general, the acute toxicities of either isoform of IL-1 were greater after intravenous compared with subcutaneous injection. Subcutaneous injection was associated with significant local pain, erythema, and swelling (Kitamura, T., & Takaku, F., *Exp. Med.* 7:170 (1989); Laughlin, M. J., *Ann. Hematol.* 67:267 (1993)). Patients receiving intravenous IL-1 at doses of 100 ng/kg or greater experienced significant hypotension. In patients receiving IL-1β from 4 to 32 ng/kg subcutaneously, there was only one episode of hypotension at the highest dose level (Laughlin, M. J., *Ann. Hematol.* 67:267 (1993)).

Contrary to IL-1-associated myelostimulation in patients with normal marrow reserves, patients with aplastic anemia treated with 5 daily doses of IL-1α (30 to 100 ng/kg) had no increases in peripheral blood counts or bone marrow cellularity (Walsh, C. E., et al., *Br. J. Haematol* 80:106 (1992)). IL-1 has been administered to patients undergoing various regiments of chemotherapy to reduce the nadir of neutropenia and thrombocytopenia.

Daily treatment with 40 ng/kg IL-1α a from day 0 to day 13 of autologous bone marrow or stem cells resulted in an earlier recovery of neutropenia (median, 12 days; P<0.001) (Weisdorf, D., et al., *Blood* 84:2044 (1994)). After 14 days of treatment, the bone marrow was significantly enriched with committed myeloid progenitor cells. Similar results were reported in patients with AML receiving 50 ng/kg/d of IL-1β for 5 days starting at the time of transplantation with purged or nonpurged bone marrow (Nemunaitis, J., et al., *Blood* 83:3473 (1994)). Injecting humans with low doses of either IL-1α or IL-1β confirms the impressive pyrogenic and hypotension-inducing properties of the molecules.

IL-1 signaling mechanisms. After binding to interleukin-1 (IL-1), the IL-1 receptor type I (IL-1RI) associates with the IL-1R Accessory Protein (IL-1RAcP) and initiates a signaling cascade that results in the activation of NF-kB, (Greenfeder, S. A., et al., *J Biol. Chem.* 270:13757–65 (1995); Sims, J. E., et al., *Science* 241:585–9 (1988); Korherr, C., et al., *Eur. J Immunol.* 27:262–7 (1997); Wesche, H., et al., *J Biol. Chem.* 272:7727–31 (1997); Freshney, N. W., et al., *Cell* 78:1039–49 (1994); and Martin, M., et al, *Eur. J Immunol.* 24:1566 (1994)). Significant similarity exists between the IL-1R signaling pathway in mammals and the Toll signaling pathway in Drosophila. Toll, which shares sequence homology with the cytoplasmic domain of the IL-1RAcP, induces Dorsal activation (a homologue of NF-kB) via the adapter protein Tube and the protein kinase Pelle, (Galindo, R. L., et al., *Development* 121:2209–18 (1995); Norris, J. L. & Manley, J. L., *Genes Devel.* 10:862–72 (1996); Letsou, A., et al., *EMBO* 12:3449–3458 (1993); and Grosshans, J., et al., *Nature* 372:563–566 (1994)); significantly the recently identified IRAK (IL-1R Associated Kinase) is homologous to Pelle, (Cao, Z., et al., *Science* 271:1128–31 (1996)). However, in mammalian cells, additional complexity is thought to exist based on the observation that multiple protein kinase activities coprecipitate with the IL-1RI (Singh, R., et al., *J Clin. Invest.* 100:419 (1997); and Eriksson, A., et al., *Cytokine* 7:649 (1995)). Furthermore, given that in Drosophila the adapter protein Tube interacts with and regulates Pelle's activity, it is likely that analogous adapter/regulatory molecules might participate in IL-1 signaling. There is a need in the art to characterize molecules involved in the IL-1 signaling pathway.

Nuclear factor kappa B (NF-kB). NF-kB is a member of a family of dimeric transcription factors made from monomers that have approximately 300 amino-acid Re1 regions which bind to DNA, interact with each other, and bind the IkB inhibitors (for review, see Baeuerle and Baltimore, *Cell* 87:13–20 (1996)). Disregulation of NF-kB has been implicated in malignant transformation and hyperplasia (Gilmore et al., *Oncogene* 9:2391–2398 (1996)). NF-kB plays an important role in the antiviral response as a virus-inducible transcriptional regulator of β-interferon, MHC class I, and inflammatory cytokine genes. NF-kB has also been shown to protect cells from pro-apoptotic stimuli (Beg et al., *Nature* 376:167–170 (1995)).

SUMMARY OF THE INVENTION

The present invention provides isolated nucleic acid molecules comprising a polynucleotide encoding the IRAK-2 polypeptide having the amino acid sequence shown in SEQ ID NO:2 or SEQ ID NO:4 or the amino acid sequence encoded by the cDNA clone deposited in a bacterial host as ATCC Deposit Number 209340 on Oct. 7, 1997.

The present invention also relates to recombinant vectors, which include the isolated nucleic acid molecules of the present invention, and to host cells containing the recombinant vectors, as well as to methods of making such vectors and host cells and for using them for production of IRAK-2 polypeptides or peptides by recombinant techniques.

The invention further provides an isolated IRAK-2 polypeptide having an amino acid sequence encoded by a polynucleotide described herein.

The present invention also provides a screening method for identifying compounds capable of enhancing or inhibiting a cellular response induced by the IRAK-2, which involves contacting cells which express the IRAK-2 with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

The invention provides a diagnostic method useful during diagnosis of a IRAK-2 or IL-1 disorder.

An additional aspect of the invention is related to a method for treating an individual in need of an increased level of IRAK-2 activity in the body comprising administering to such an individual a composition comprising a therapeutically effective amount of an isolated IRAK-2 polypeptide of the invention or an agonist thereof.

A still further aspect of the invention is related to a method for treating an individual in need of a decreased level of IRAK-2 activity in the body comprising, administering to such an individual a composition comprising a therapeutically effective amount of an IRAK-2 antagonist.

BRIEF DESCRIPTION OF THE FIGURES

FIGS. 1A-C shows the nucleotide (SEQ ID NO:1) and deduced amino acid (SEQ ID NO:2) sequences of IRAK-2α. The protein has a deduced molecular weight of about 65 kDa.

FIGS. 2A-D shows the nucleotide (SEQ ID NO:3) and deduced amino acid (SEQ ID NO:4) sequences of IRAK-2β.

FIGS. 3A-B shows the regions of similarity between the amino acid sequences of the IRAK-2α (SEQ ID NO:2) and IRAK-2β (SEQ ID NO:4) proteins and human IRAK (SEQ ID NO:5) and Pelle (SEQ ID NO:6). Alignment was performed with Custall software.

FIG. 4.

FIG. 6.

FIGS. 8A–C show that MyD88 dominant negative version, MyD88 (152–296), abrogates IL-1Rs-induced but not IRAK-2-induced NF-kB activity. Conversely IRAK-2 dominant negative versions, IRAK-2 (1–96) and IRAK-2 (97–590), significantly inhibit both IL-1RS and MyD88-induced NF-kB activity. 0.2 μg of inducer and 0.6 μg of dominant negative expression constructs were used in each transfection. Data are expressed as percentage of relative induced NF-kB activity.

DETAILED DESCRIPTION

Figure 4A:
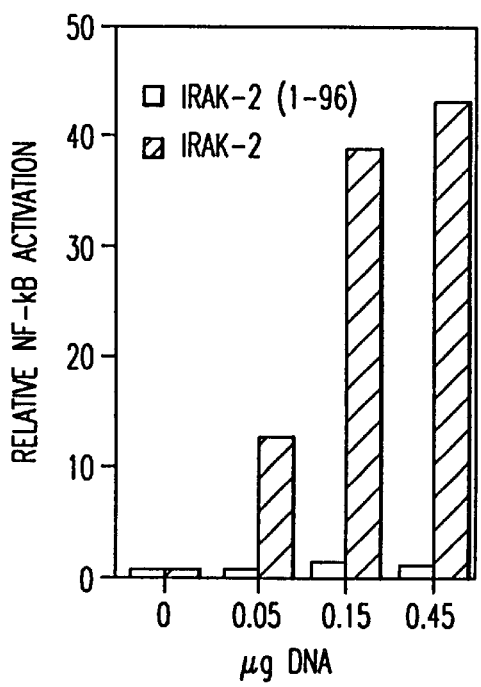
FIG. 4A shows that ectopic expression of IRAK-2 but not the mutant version of IRAK-2 (1–96) activates NF-kB in 293 cells as measured by NF-kB reporter gene activity.

The present inventors have identified a human IRAK-2, IRAK-2α, and a splice variant thereof, IRAK-2β. Thus, the present invention provides isolated nucleic acid molecules comprising a polynucleotide encoding an IRAK-2 polypeptide having the amino acid sequence shown in SEQ ID NO:2. The present invention also provides isolated nucleic acid molecules comprising a polynucleotide encoding an IRAK-2 polypeptide having the amino acid sequence shown in SEQ ID NO:4, which was determined by sequencing a cloned cDNA. The IRAK-2α and IRAK-2β proteins of the present invention shares sequence homology with IRAK (SEQ ID NO:5) and Pelle (SEQ ID NO:6). The nucleotide sequence shown in SEQ ID NO:3 was obtained by sequencing a cDNA clone, which was deposited on Oct. 7, 1997 at the American Type Culture Collection, 10801 University Blvd. Manassar, Va. 20110–2209, U.S.A. and given accession number 209340. The deposited clone is inserted in the pBluescript SK(−) plasmid (Stratagene, LaJolla, Calif.) using the EcoRI and XhoI restriction endonuclease cleavage sites.

Nucleic Acid Molecules

Unless otherwise indicated, all nucleotide sequences determined by sequencing a DNA molecule herein were determined using an automated DNA sequencer, and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in SEQ ID NO:1 or SEQ ID NO:3, a nucleic acid molecule of the present invention encoding an IRAK-2 polypeptide may be obtained using standard cloning and screening procedures, such as those for cloning cDNAs using mRNA as starting material. Illustrative of the invention, the nucleic acid molecule described in SEQ ID NO:1 was discovered in a cDNA library derived from HUVEC cells. The determined nucleotide sequence of the IRAK-2 cDNA of SEQ ID NO:1 contains an open reading frame encoding a protein of about 590 amino acid residues and a deduced molecular weight of about 65 kDa. The nucleic acid molecule described in SEQ ID NO:3 was discovered in cDNA libraries derived from HUVEC cells and activated neutrophils. The determined nucleotide sequence of the IRAK-2 cDNA of SEQ ID NO:3 contains an open reading frame encoding a protein of about 625 amino acids. The IRAK-2 proteins shown in SEQ ID NO:2 and SEQ ID NO:4 are about 35–40 % identical and about 50–60 % similar to IRAK (SEQ ID NO:5).

As one of ordinary skill would appreciate, due to the possibilities of sequencing errors, the predicted IRAK-2 polypeptide encoded by the deposited cDNA comprises about 625 amino acids, but may be anywhere in the range of 600–650 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) shown in SEQ ID NO:1 or SEQ ID NO:3; and DNA molecules which comprise a sequence substantially different from those described above but which, due to the degeneracy of the genetic code, still encode an IRAK-2 protein. Of course, the genetic code is well known in the art. Thus, it would be routine for one skilled in the art to generate such degenerate variants.

In addition, the present inventors have identified the following cDNA clones related to extensive portions of SEQ ID NO:1 and SEQ ID NO:3: HPMCW18R (SEQ ID NO:7), HTADQ88R (SEQ ID NO:8), HNFEL57R (SEQ ID NO:9), HAPCM54R (SEQ ID NO:10), HNFFX36R (SEQ ID NO:11), HNFHL91R (SEQ ID NO:12), and HCE5L53R (SEQ ID NO:13).

The following public EST, which relates to portions of SEQ ID NO:1 and SEQ ID NO:3, has also been identified: Genbank Accession No. N52479, (SEQ ID NO:14).

In another aspect, the invention provides isolated nucleic acid molecules encoding the IRAK-2 polypeptide having an amino acid sequence as encoded by the cDNA clone contained in the plasmid deposited as ATCC Deposit No. 209340 on Oct. 7, 1997. In a further embodiment, nucleic acid molecules are provided encoding the full-length IRAK-2α or IRAK-1β polypeptide lacking the N-terminal methionine. The invention also provides an isolated nucleic acid molecule having the nucleotide sequence shown in SEQ ID NO:1 or SEQ ID NO:3 or the nucleotide sequence of the IRAK-2 cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the IRAK-2 gene in human tissue, for instance, by Northern blot analysis.

The present invention is further directed to fragments of the isolated nucleic acid molecules described herein. By a fragment of an isolated nucleic acid molecule having the nucleotide sequence of the deposited cDNA or the nucleotide sequence shown in SEQ ID NO:1 or SEQ ID NO:3 is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, or 1700 nt in length are also useful according to the present invention as are fragments corresponding to most, if not all, of the nucleotide sequence of the deposited cDNA or as shown in SEQ ID NO:1 or SEQ ID NO:3. By a fragment at least 20 nt in length, for example, is intended fragments which include 20 or more contiguous bases from the nucleotide sequence of the deposited cDNA or the nucleotide sequence as shown in SEQ ID NO:1 or SEQ ID NO:3.

Preferred nucleic acid fragments of the present invention include nucleic acid molecules encoding epitope-bearing portions of the IRAK-2 protein. In particular, such nucleic acid fragments of the present invention include nucleic acid molecules encoding: a polypeptide comprising amino acid residues from about 96 to about 193 in SEQ ID NO:2 or SEQ ID NO:4; a polypeptide comprising amino acid residues from about 207 to about 254 in SEQ ID NO:2 or SEQ ID NO:4; a polypeptide comprising amino acid residues from about 293 to about 316 in SEQ ID NO:2 or SEQ ID NO:4; a polypeptide comprising amino acid residues from about 416 to about 472 in SEQ ID NO:2 or SEQ ID NO:4; a polypeptide comprising amino acid residues from about 487 to about 541 in SEQ ID NO:2 or SEQ ID NO:4; and a polypeptide comprising amino acid residues from about 559 to about 619 in SEQ ID NO:4. The inventors have determined that the above polypeptide fragments are antigenic regions of the IRAK-2 polypeptides. Methods for determining other such epitope-bearing portions of the IRAK-2 protein are described in detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit 209340. By "stringent hybridization conditions" is intended overnight incubation at 42° C. in a solution comprising:50% formamide, 5×SSC (1750 nM NaCL 75 mM trisodium citrate), 50 mM sodium phosphate (pH 7.6), 5× Denhardt's solution, 10% dextran sulfate, and 20 mg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in SEQ ID NO:1 or SEQ ID NO:3). Of course, a polynucleotide which hybridizes only to a poly A sequence (such as the 3' terminal poly(A) tract of the IRAK-2 cDNA shown in SEQ ID NO:1 or SEQ ID NO:3), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode an IRAK-2 polypeptide may include, but are not limited to those encoding the amino acid sequence of the full-length polypeptide, by itself; the coding sequence for the full-length polypeptide and additional sequences, such as those encoding a leader or secretory sequence, such as a pre-, or pro- or prepro-protein sequence; the coding sequence of the full-length polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example— ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767–778 (1984). As discussed below, other such fusion proteins include the IRAK-2 fused to Fc at the N- or C-terminus.

The present invention further relates to variants of the nucleic acid molecules of the present invention, which encode portions, analogs or derivatives of the IRAK-2 protein. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the IRAK-2 protein or portions thereof. Also especially preferred in this regard are conservative substitutions.

Further embodiments of the invention include isolated nucleic acid molecules comprising apolynucleotide having a nucleotide sequence at least 95% identical, and more preferably at least 96%, 97%, 98% or 99% identical to (a) a nucleotide sequence encoding the polypeptide having the amino acid sequence in SEQ ID NO:2; (b) a nucleotide sequence encoding the polypeptide having the amino acid sequence in SEQ ID NO:2, but lacking the N-terminal methionine; (c) a nucleotide sequence encoding the polypeptide having the amino acid sequence in SEQ ID NO:4; (d) a nucleotide sequence encoding the polypeptide having the amino acid sequence in SEQ ID NO:4, but lacking the N-terminal methionine; (e) a nucleotide sequence encoding the polypeptide having the amino acid sequence encoded by the cDNA clone contained in ATCC Deposit No. 209340; (f) a nucleotide sequence encoding the IRAK-2 polypeptide having the amino acid sequence encoded by the cDNA clone contained in ATCC Deposit No. 209340, but lacking the N-terminal methionine; or (g) a nucleotide sequence complementary to any of the nucleotide sequences in (a), (b), (c), (d), (e), or (f).

By a polynucleotide having a nucleotide sequence at least, for example, 95% "identical" to a reference nucleotide sequence encoding a IRAK-2 polypeptide is intended that the nucleotide sequence of the polynucleotide is identical to the reference sequence except that the polynucleotide sequence may include up to five point mutations per each 100 nucleotides of the reference nucleotide sequence encoding the IRAK-2 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequence shown in SEQ ID NO:1 or SEQ ID NO:3 or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 95%, 96%, 97%, 98% or 99% identical to the nucleic acid sequence shown in SEQ ID NO:1 or SEQ ID NO:3 or to the nucleic acid sequence of the deposited cDNA, irrespective of whether they encode a polypeptide having IRAK-2 activity. This is because even where a particular nucleic acid molecule does not encode a polypeptide having IRAK-2 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having IRAK-2 activity include, inter alia, (1) isolating the IRAK-2 gene or allelic variants thereof in a cDNA library; (2) in situ hybridization (e.g., "FISH") to metaphase chromosomal spreads to provide precise chromosomal location of the IRAK-2 gene, as described in Verma et al., *Human Chromosomes: A Manual of Basic Techniques,* Pergamon Press, New York (1988); and (3) Northern Blot analysis for detecting IRAK-2 mRNA expression in specific tissues.

Preferred, however, are nucleic acid molecules having sequences at least 95%, 96%, 97%, 98% or 99% identical to a nucleic acid sequence shown in SEQ ID NO:1 or SEQ ID NO:3 or to a nucleic acid sequence of the deposited cDNA which do, in fact, encode a polypeptide having IRAK-2 protein activity. By "a polypeptide having IRAK-2 activity" is intended polypeptides exhibiting IRAK-2 activity in a particular biological assay. For example, IRAK-2 protein activity can be measured using the luciferase assay described in Cao et al., *Nature* 383:443–446 (1996) and below in Example 1.

Briefly, cells which have been transfected with a nucleic acid encoding for a candidate polypeptide, such as human 293 cells, are transfected with an ELAM-1-luciferase reporter plasmid. Luciferase activity is measured in these cells and compared to cells which have been transfected with the luciferase construct, but not with the candidate polypeptide. A higher level of luciferase activity in cells with the candidate polypeptide is indicative of IRAK-2 activity.

Of course, due to the degeneracy of the genetic code, one of ordinary skill in the art will immediately recognize that a large number of the nucleic acid molecules having a sequence at least 95%, 96%, 97%, 98%, or 99% identical to a nucleic acid sequence of the deposited cDNA or a nucleic acid sequence shown in SEQ ID NO:1 or SEQ ID NO:3 will encode a polypeptide "having IRAK-2 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having IRAK-2 protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that proteins are surprisingly tolerant of amino acid substitutions.

Vectors and Host Cells

The present invention also relates to vectors which include the isolated DNA molecules of the present invention, host cells which are genetically engineered with the recombinant vectors, and the production of IRAK-2 polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli,* Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL-5. See, D. Bennett et al., *Journal of Molecular Recognition,* Vol.8:52–58 (1995) and K. Johanson et al., *The Journal of Biological Chemistry,* Vol. 270, No. 16:9459–9471(1995).

The IRAK-2 protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

IRAK-2 Polypeptides and Fragments

The invention further provides an isolated IRAK-2 polypeptide having the amino acid sequence encoded by the deposited cDNA, or the amino acid sequence in SEQ ID NO:2, or the amino acid sequence in SEQ ID NO:4, or a peptide or polypeptide comprising a portion of the above polypeptides.

It will be recognized in the art that some amino acid sequences of the IRAK-2α or IRAK-1β polypeptides can be varied without significant effect of the structure or function of the protein. If such differences in sequence are contemplated, it should be remembered that there will be critical areas on the protein which determine activity.

Thus, the invention further includes variations of the IRAK-2α or IRAK-1β polypeptide which show substantial IRAK-2 polypeptide activity or which include regions of IRAK-2 protein such as the protein portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247:1306–1310 (1990).

Thus, the fragment, derivative or analog of the polypeptide of SEQ ID NO:2 or SEQ ID NO:4, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the IRAK-2 protein. The prevention of aggregation is highly desirable. Aggregation of proteins not only results in a loss of activity but can also be problematic when preparing pharmaceutical formulations, because they can be immunogenic. (Pinckard et al., *Clin. Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above. Generally speaking, the number of amino acid substitutions for any given IRAK-2 polypeptide will not be more than 50, 40, 30, 20, 10, 5 or 3.

Amino acids in the IRAK-2 proteins of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as in vitro proliferative activity.

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell or a native source. For example, a recombinantly produced version of the IRAK-2 polypeptide can be substantially purified by the one-step method described in Smith and Johnson, *Gene* 67:31–40 (1988).

The polypeptides of the present invention include the a polypeptide comprising the polypeptide encoded by the deposited cDNA; a polypeptide comprising the polypeptide encoded by the deposited cDNA, but minus the N-terminal methionine; a polypeptide comprising amino acids about 1 to about 590 in SEQ ID NO:2; a polypeptide comprising amino acids about 2 to about 590 in SEQ ID NO:2; a polypeptide comprising amino acids about 1 to about 625 in SEQ ID NO:4; a polypeptide comprising amino acids about 2 to about 625 in SEQ ID NO:4; as well as polypeptides which are at least 95% identical, and more preferably at least 96%, 97%, 98% or 99% identical to those described above and also include portions of such polypeptides with at least 30 amino acids and more preferably at least 50 amino acids.

By a polypeptide having an amino acid sequence at least, for example, 95% "identical" to a reference amino acid sequence of a IRAK-2 polypeptide is intended that the amino acid sequence of the polypeptide is identical to the reference sequence except that the polypeptide sequence may include up to five amino acid alterations per each 100 amino acids of the reference amino acid of the IRAK-2 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to, for instance, the amino acid sequence shown in SEQ ID NO:2 or SEQ ID NO:4 or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention are useful as a molecular weight marker on SDS-PAGE gels or on molecular sieve gel filtration columns using methods well known to those of skill in the art.

In another aspect, the invention provides a peptide or polypeptide comprising an epitope-bearing portion of a polypeptide of the invention. The epitope of this polypeptide portion is an immunogenic or antigenic epitope of a polypeptide described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. *Science* 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767–778 (1984) at 777.

Antigenic epitope-bearing peptides and polypeptides of the invention preferably contain a sequence of at least seven, more preferably at least nine and most preferably between about at least about 15 to about 30 amino acids contained within the amino acid sequence of a polypeptide of the invention.

Non-limiting examples of antigenic polypeptides or peptides that can be used to generate IRAK-2-specific antibodies include: a polypeptide comprising amino acid residues from about 96 to about 193 in SEQ ID NO:2 or SEQ ID NO:4; a polypeptide comprising amino acid residues from about 207 to about 254 in SEQ ID NO:2 OR SEQ ID NO:4; a polypeptide comprising amino acid residues from about 293 to about 316 in SEQ ID NO:2 or SEQ ID NO:4; a polypeptide comprising amino acid residues from about 416 to about 472 in SEQ ID NO:2 or SEQ ID NO:4; a polypeptide comprising amino acid residues from about 487 to about 541 in SEQ ID NO:2 or SEQ ID NO:4; and a polypeptide comprising amino acid residues from about 559 to about 619 in SEQ ID NO:4. As indicated above, the inventors have determined that the above polypeptide fragments are antigenic regions of the IRAK-2 protein.

The epitope-bearing peptides and polypeptides of the invention may be produced by any conventional means. Houghten, R. A. (1985) General method for the rapid solid-phase synthesis of large numbers of peptides: specificity of antigen-antibody interaction at the level of individual amino acids. *Proc. Natl. Acad. Sci. USA* 82:5131–5135. This "Simultaneous Multiple Peptide Synthesis (SMPS)" process is further described in U.S. Pat. No. 4,631,211 to Houghten et al. (1986).

As one of skill in the art will appreciate, IRAK-2 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than the monomeric IRAK-2 protein or protein fragment alone (Fountoulakis et al., *J Biochem* 270:3958–3964 (1995)).

Screening Assays

The present inventors have shown that IRAK-2 mediates NF-kB activation induced by IL-1R stimulation. NF-kB is an ubiquitous transcription factor which has been shown to activate transcription of enzymes, such as cyclooxygenase-2 (Newton et al., *Biochem. Biophys. Res. Commun.* 237(1):28–32 (1997)); cytokines, such as RANTES (Moriuchi et al., *J Immunol.* 158(7):3483–3491 (1997)); adhesion molecules, such as E-selectin (ELAM-1) (Read et al., *J. Biol. Chem.* 272(5):2753–2761 (1997)); and other molecules. The normal functions of NF-kB include communication between cells, embryonal development, the response to stress, inflammation and viral infection, and the maintenance of cell type specific expression of genes (for review, see Wulczyn et al., *J. Mol. Med* 74(12):749–769 (1996)). Upregulation of NF-kB could be used to treat viral infections, such as HIV ((Moriuchi et al., *J. Immunol.* 158(7):3483–3491 (1997)), and damage caused by oxidative stress (Renard et al., *Biochem. Pharmacol.* 53:149–160 (1997)). Disregulation of NF-kB activation has been linked to adult respiratory distress syndrome, sepsis syndrome, asthma, rheumatoid arthritis, inflammatory bowel disease, malignant transformation and hyperplasia (Blackwell et al., *Am. J Respir. Cell. Mol. Biol.* 17(1):3–9 (1997); Barnes, *Int. J. Biochem. Cell. Biol.* 29(6):867–870 (1997); and Gilmore et al., *Oncogene* 9:2391–2398(1996)). Accordingly, inhibitors of NF-kB could be used to treat these disorders. Several inhibitors of NF-kB have been identified, including antioxidants such as alpha-tocopherol (Erl et al., *Am. J. Physiol.* 273:H634–H640 (1997)), and glucocorticoids, such as dexamethasone (Wang et al., *J. Immunol.* 159:534–537 (1997))).

Thus, the present invention also provides a screening method for determining whether a compound of interest is an agonist or antagonist of the IRAK-2 pathway. This method involves contacting cells which express IRAK-2, either exogenously or endogenously, with a compound of interest, assaying NF-kB mediated transcription, and comparing the NF-kB mediated transcription to a standard response. The standard response is the level of NF-kB mediated transcription in cells expressing IRAK-2 that have not been contacted with the compound of interest, whereby an increase in NF-kB mediated transcription over the standard indicates that the compound of interest is an agonist of the IRAK-2 pathway and a decrease in NF-kB mediated transcription under the standard indicates that the compound of interest is an antagonist of the IRAK-2 pathway.

By "assaying NF-kB mediated transcription" is intended qualitatively or quantitatively measuring NF-kB mediated transcription. By the invention, the compound of interest is an agonist of the IRAK-2 pathway if NF-kB mediated transcription is enhanced over that observed due to IRAK-2 in the absence of the compound of interest and the compound of interest is an antagonist of the IRAK-2 pathway if NF-kB mediated transcription is diminished compared to that observed due to IRAK-2 in the absence of the compound of interest. Since IRAK-2 activates NF-kB transcription, any in vitro or in vivo assay which measures NF-kB activity can be used in this method.

For example, a construct encoding for IRAK-2 is transfected into a cell, along with a construct containing a reporter gene which is under the control of a promoter which is activated in the presence of NF-kB. Any reporter gene which is known in the art can be used in this assay. Examples of reporter genes useful in this assay include, but are not limited to, luciferase, β-galactosidase, and chloramphenicol acetyltransferase. NF-kB-responsive promoters can include one or more binding sites for NF-kB. Examples of promoters which are sensitive to NF-kB include, but are not limited to, the promoter for ELAM-1 and the promoter for RANTES. After transfection of the constructs, the cell is contacted with a compound of interest, and the reporter gene expression is measured and compared to the reporter gene expression seen in cells which have not been contacted with the compound of interest. An increase in reporter gene expression in cells which have been contacted with the compound of interest indicates that the compound is an agonist of the IRAK-2 pathway. A decrease in reporter gene expression in cells which have been contacted with the compound of interest indicates that the compound is an antagonist of the IRAK-2 pathway.

IRAK-2 Related Disorder Diagnosis

For IRAK-2 related disorders, it is believed that substantially altered (increased or decreased) levels of IRAK-2 gene expression can be detected in tissues taken from a mammal having such a disorder, relative to a "standard" mammal, i.e., a mammal of the same species not having the disorder. Thus, the invention provides a diagnostic method useful during diagnosis of an IRAK-2 related disorder, which involves assaying the expression level of the gene encoding the IRAK-2 protein in mammalian cells or body fluid and comparing the gene expression level with a standard IRAK-2 gene expression level, whereby an increase in the gene expression level over the standard is indicative of certain disorders.

IRAK-2 related disorders are believe to include, but are not limited to, leukemia, lymphoma, rheumatoid arthritis, sarcoidosis, tuberculosis, onchocerciasis, allergies, various bacterial infections, arteriosclerosis, autoimmune diseases, and inflammatory diseases.

Where a diagnosis has already been made according to conventional methods, the present invention is useful as a prognostic indicator, whereby patients exhibiting enhanced IRAK-2 gene expression will experience a worse clinical outcome relative to patients expressing the gene at a lower level.

By "assaying the expression level of the gene encoding the IRAK-2 protein" is intended qualitatively or quantitatively measuring or estimating the level of the IRAK-2 protein or the level of the mRNA encoding the IRAK-2 protein in a first biological sample either directly (e.g., by determining or estimating absolute protein level or mRNA level) or relatively (e.g., by comparing to the IRAK-2 protein level or mRNA level in a second biological sample).

Preferably, the IRAK-2 protein level or mRNA level in the first biological sample is measured or estimated and compared to a standard IRAK-2 protein level or mRNA level, the standard being taken from a second biological sample obtained from an individual not having the disorder. As will be appreciated in the art, once a standard IRAK-2 protein level or mRNA level is known, it can be used repeatedly as a standard for comparison.

By "biological sample" is intended any biological sample obtained from an individual, cell line, tissue culture, or other source which contains IRAK-2 protein or mRNA. Biological samples include mammalian body fluids (such as sera, plasma, urine, synovial fluid and spinal fluid) which contain IRAK-2 protein, and ovarian, prostate, heart, placenta, pancreas liver, spleen, lung, breast and umbilical tissue.

Preferred mammals include monkeys, apes, cats, dogs, cows, pigs, horses, rabbits and humans. Particularly preferred are humans.

Total cellular RNA can be isolated from a biological sample using the single-step guanidinium-thiocyanate-phenol-chloroform method described in Chomczynski and Sacchi,*Anal. Biochem.* 162:156–159(1987). Levels of mRNA encoding the IRAK-2 protein are then assayed using any appropriate method. These include Northern blot analysis (Harada et al., *Cell* 63:303–312 (1990)), S1 nuclease mapping (Fujita et al., *Cell* 49:357–367 (1987)), the polymerase chain reaction (PCR), reverse transcription in combination with the polymerase chain reaction (RT-PCR) (Makino et al., *Technique* 2:295–301 (1990)), and reverse transcription in combination with the ligase chain reaction (RT-LCR).

Assaying IRAK-2 protein levels in a biological sample can occur using antibody-based techniques. For example, IRAK-2 protein expression in tissues can be studied with classical immunohistological methods (Jalkanen, M., et al., *J. Cell. Biol.* 101:976–985 (1985); Jalkanen, M., et al., *J. Cell . Biol.* 105:3087–3096 (1987)).

Other antibody-based methods useful for detecting IRAK-2 protein gene expression include immunoassays, such as the enzyme linked immunosorbent assay (ELISA) and the radioimmunoassay (RIA).

Suitable labels are known in the art and include enzyme labels, such as, Glucose oxidase, and radioisotopes, such as iodine ($^{125}I$, $^{121}I$), carbon ($^{14}C$), sulfur ($^{35}S$), tritium ($^{3}H$), indium ($^{112}In$ ), and technetium ($^{99m}Tc$), and fluorescent labels, such as fluorescein and rhodamine, and biotin.

Modes of Administration

It will be appreciated that conditions caused by a decrease in the standard or normal level of IRAK-2 activity in an individual can be treated by administration of IRAK-2 protein. Thus, the invention further provides a method of treating an individual in need of an increased level of IRAK-2 activity comprising administering to such an individual a pharmaceutical composition comprising an effective amount of an isolated IRAK-2 polypeptide of the invention effective to increase the IRAK-2 activity level in such an individual.

As a general proposition, the total pharmaceutically effective amount of IRAK-2 polypeptide administered parenterally per dose will be in the range of about 1 μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the IRAK-2 polypeptide is typically administered at a dose rate of about 1 μg/kg/hour to about 50 μg/kg/hour, either by 1–4 injections per day or by continuous subcutaneous infusions, for example, using a mini-pump. An intravenous bag solution may also be employed.

Pharmaceutical compositions containing the IRAK-2 of the invention may be administered orally, rectally, parenterally, intracisternally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Chromosome Assays

The nucleic acid molecules of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, the cDNA herein disclosed is used to clone genomic DNA of a IRAK-2 protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3′ untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques,* Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man,* available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1

Characterization of IRAK-2α

A novel partial human cDNA was identified that showed significant homology to both IRAK and Pelle. Screening of a human HUVEC cDNA library resulted in the isolation of a full length cDNA clone; analysis of the nucleotide sequence revealed an open reading frame encoding a 590 amino acids (aa) protein with a calculated MW of 65 kDa (FIG. 1). Clustall alignment analysis showed significant homology to both IRAK and Pelle (FIG. 3). Given its sequence and functional similarity to IRAK the molecule was designated IRAK-2. Northern blot analysis revealed a single IRAK-2 transcript expressed in a variety of tissues whose size (about 4 Kbp) was consistent with that of the cDNA.

Figure 4B:
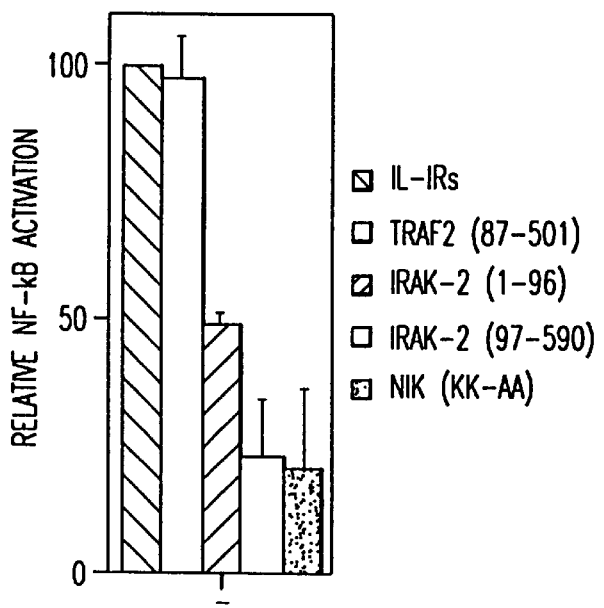
FIG. 4B shows that IRAK-2 (1–96) and IRAK-2 (97–590) inhibit IL-1Rs-induced NF-kB activity. Transfection with TRAF-2 (87–501) and NIK (KK429–430AA) expression vectors served as negative and positive controls, respectively. 0.1 μg of IL-1RI plus 0.1 μg of IL-1RAcP and 0.6 μg of putative inhibitory expression constructs were transfected. Data are expressed as percentage of relative IL-1Rs-induced NF-kB activity.

Ectopic expression of IRAK-2 in human 293 cells induced NF-kB activation as determined by relative luciferase activity of a NF-kB responsive construct. Truncated versions of IRAK-2 encoding amino acid residues 1 to 96 of SEQ ID NO:2 [IRAK-2 (1–96)] or amino acid residues 97 to 590 of SEQ ID NO:2 [IRAK-2 (97–590)] failed to induce any luciferase activity suggesting that integrity of the molecule was essential for its function (FIG. 4A). Deletional analysis has previously shown that a mutant version of Pelle analogous to IRAK-2 (97–590) is also inactive leading to the suggestion that Pelle's recruitment to the plasma membrane through its N-terminal domain is necessary for its subsequent function (Galindo, R. L., et al., *Development* 121:2209–2218 (1995)). Given this, it was tested whether IRAK-2 (1–96) or IRAK-2 (97–590) could act as dominant negative inhibitors of IL-1R-induced NF-kB activity. Coexpression of IL-1RI and IL-1RAcP (IL-1Rs for clarity) strongly induced NF-kB activity. Surprisingly, both IRAK-2 (1–96) and IRAK-2 (97–590) inhibited IL-1Rs-induced NF-kB activity. A dominant negative mutant version of the downstream kinase NIK that is implicated in IL-1R-induced NF-kB activation was used as a positive control; the unrelated adapter molecule TRAF2 (298–522) was used as a negative control (FIG. 4B).

Given the sequence similarity shared by IRAK and IRAK-2, and the functional involvement of IRAK-2 in IL-1Rs-induced NF-kB activity, it was analyzed whether IRAK-2 was recruited to the IL-1R signaling complex. Interestingly, while IRAK preferentially coprecipitated with IL-1RAcP, IRAK-2 preferentially bound to the IL-1RI. In contrast, a mutant version of IRAK-2 lacking the first 96 amino acid residues [IRAK-2 (97–590)] failed to associate with IL-1RI suggesting that its N-terminal domain docks with the cytoplasmic domain of IL-1RI. Confirming this was the finding that a truncated form of IRAK-2 coding for the first 96 amino acid residues [IRAK-2 (1–96)] specifically coprecipitated with IL-1RI.

Figure 5:
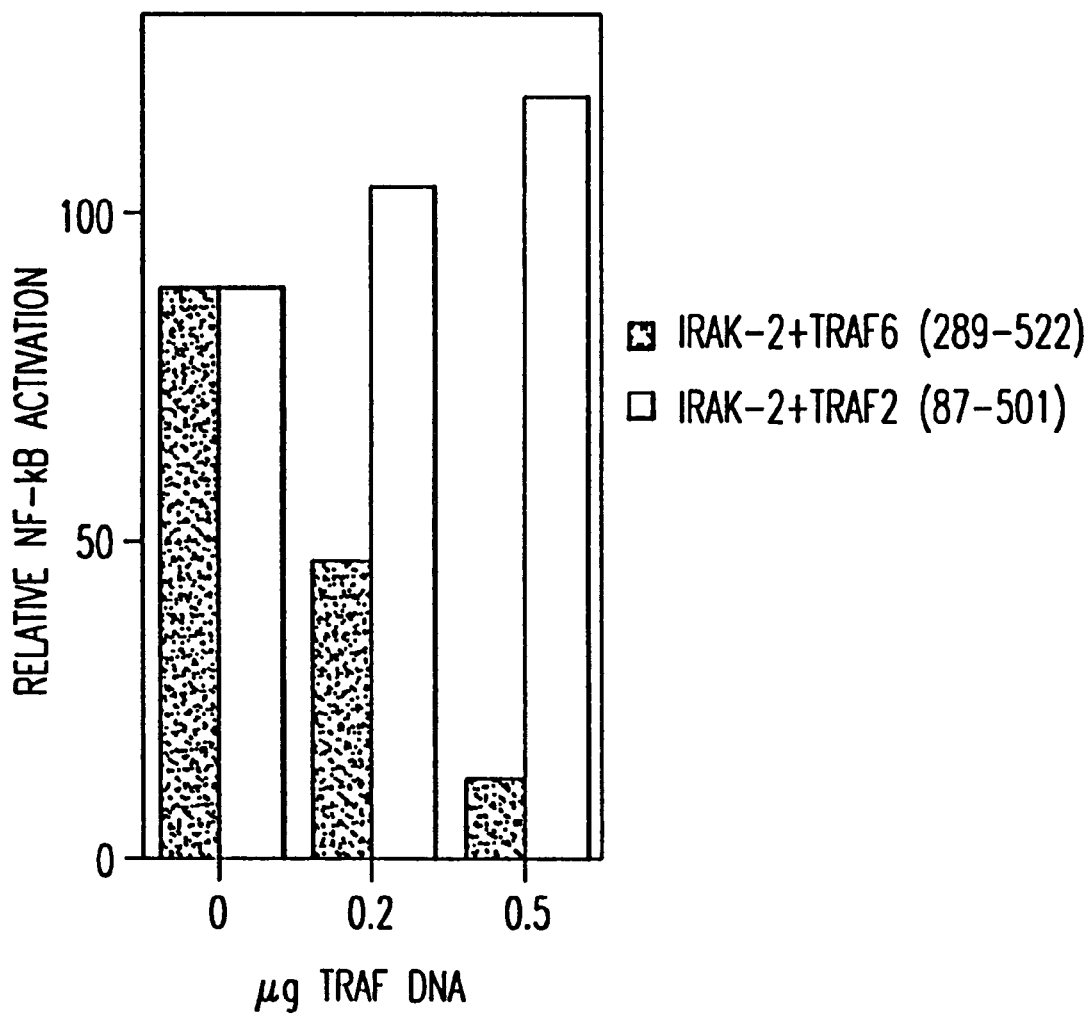
FIG. 5 shows that IRAK-2 induced NF-kB activity is specifically abrogated by TRAF6 (289–522) but not TRAF2 (87–501). 293 cells were transfected with 0.2 μg of IRAK-2 and increasing amounts of TRAF constructs.

Certain members of the TRAF adapter family mediate NF-kB activation induced by a number of cytokine receptors. TRAF2, for example plays a critical role in TNFR1 and –2 mediated NF-kB activation. TRAF6 has recently been implicated in the IL-1 signaling pathway and shown to complex with IRAK (Cao, Z., et al., *Nature* 383:443–6 (1996)). It was therefore determined if IRAK-2 interacted with TRAF6 when coexpressed in 293T cells. Both IRAK and IRAK-2 coprecipitated with TRAF6 but not with the related TRAF2. A dominant negative version of TRAF6 [TRAF6 (298–522)] which inhibits IL-1-induced NF-kB activity, also bound both IRAK and IRAK-2. Further, IRAK-2-induced NF-kB activity was specifically inhibited by dominant negative TRAF6 (298–522) but not by a dominant negative version of TRAF2 [TRAF2 (87–501)] (FIG. 5). These data are in keeping with TRAF6 acting downstream of IRAK-2, in the IL-1 mediated NF-kB signaling pathway.

Additional putative proximally participating adapters/regulators were sought by systematically looking for proteins showing homology to either Tube or IL-1RAcP. BLAST searches of the public data base revealed the cytoplasmic domain of the IL-1RAcP to possess significant homology to MyD88 (Lord, K., et al., *Oncogene* 5:1095 (1990)). Sequence similarity between MyD88, IL-1RI and Toll has previously been reported, but the functional significance of this homology has been obscure. Interestingly, the MyD88 polypeptide has a modular structure composed of two fused module types: a N-terminal "interaction domain" (or DD for Death Domain that was initially defined in proteins involved in programmed cell death), (Feinstein, E., et al., *Trends Biochem. Sci.* 20:342–4 (1995); and Hofmann, K. & Tschopp, J., et al., *FEBS Letters* 371:321 (1995)) and a C-terminal domain related to the cytoplasmic region of IL-1RAcP, IL-1RI, Toll and the recently identified human Toll homologue (Hardiman, G., et al., *Oncogene* 13:2467–75 (1996); Hultmark, D., *Biochem. Biophys. Res. Commun.* 199:144 (1994); Bonnert, T., et al., *FEBS lett.* 402:81–84 (1997); and Medzhitov, R., et al., *Nature* 388:394 (1997)). Given the presence of these two distinct domains it was hypothesized that MyD88 might simultaneously connect a transmembrane receptor belonging to the IL-1R family with a downstream signaling mediator. To test this, the role of human MyD88 was functionally characterized.

Figure 6A:
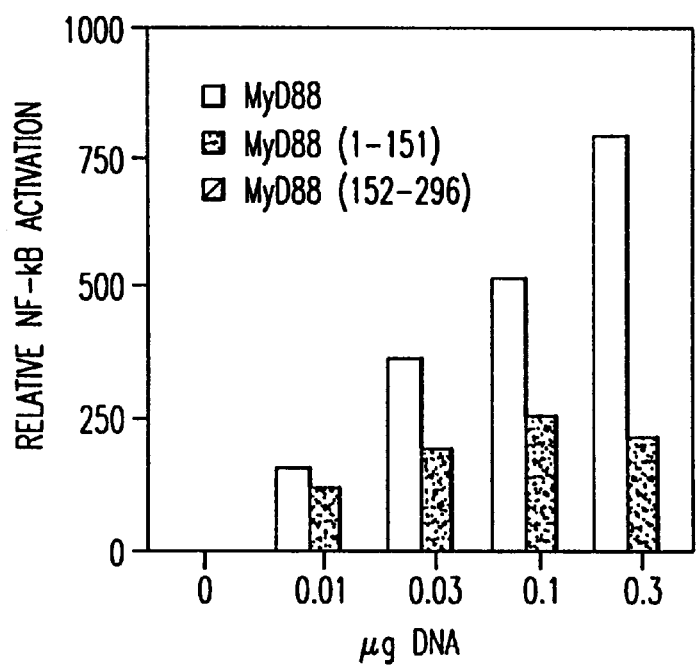
FIG. 6A shows that ectopic expression of MyD88 in 293 cells results in the induction of NF-kB activity. A mutant version of MyD88 encoding a N-terminal region, MyD88 (1–152), was similarly capable of inducing NF-kB activity albeit to a lesser extent; in contrast a mutant version of MyD88 coding for amino acids 152 to the end, MyD88 (152–296) failed to induce any luciferase activity (not evident in graph).
Figure 6B:
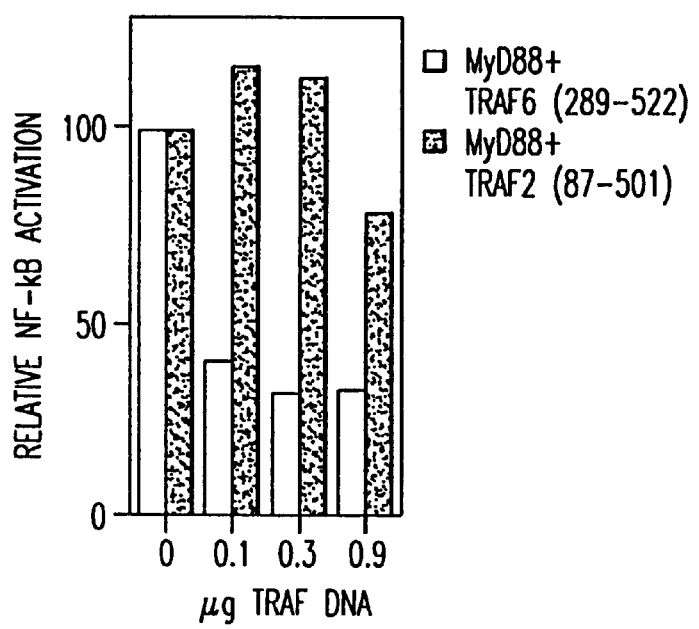
FIG. 6B shows that MyD88-induced NF-kB activity was selectively inhibited by a dominant negative version of TRAF6, TRAF6 (298–522) but not TRAF2 (87–501). 0.1 μg of MyD88 and increasing amount of TRAF expression constructs were used. Data are expressed as percentage of relative MyD88-induced NF-kB activity.

Ectopic expression of MyD88 in 293 cells strongly induced NF-kB activity in a dose dependent manner. Similarly, a truncated version of MyD88 encoding the N-terminal domain (DD), MyD88 (1–151), activated NF-kB albeit to a lesser extent. In contrast, the C-terminal region, MyD88 (152–296) did not induce any luciferase activity (FIG. 6A). Significantly, MyD88-induced NF-kB activity was specifically inhibited by TRAF6 but not TRAF2 dominant negative expression constructs suggesting that TRAF6 and MyD88 likely participate in the same signaling pathway and that TRAF6 functions downstream of MyD88 (FIG. 6B). It was next tested whether MyD88 (152–296) could act as a dominant negative inhibitor of IL-1Rs-induced NF-kB activity; MyD88 (152–296) specifically inhibited IL-1Rs-induced but not TNFR2-induced NF-kB activation. A dominant negative version of TRAF6 [TRAF6 (289–522)] similarly inhibited IL-1Rs-induced but not TNFR2-induced NF-kB activation; in contrast, a dominant negative version of TRAF2 [TRAF2 (87–501)] abrogated TNFR2-induced, induced, but not IL-1Rs-induced, NF-kB activity confirming the specificity of effects observed with MyD88 (152–296).

Figure 7A:
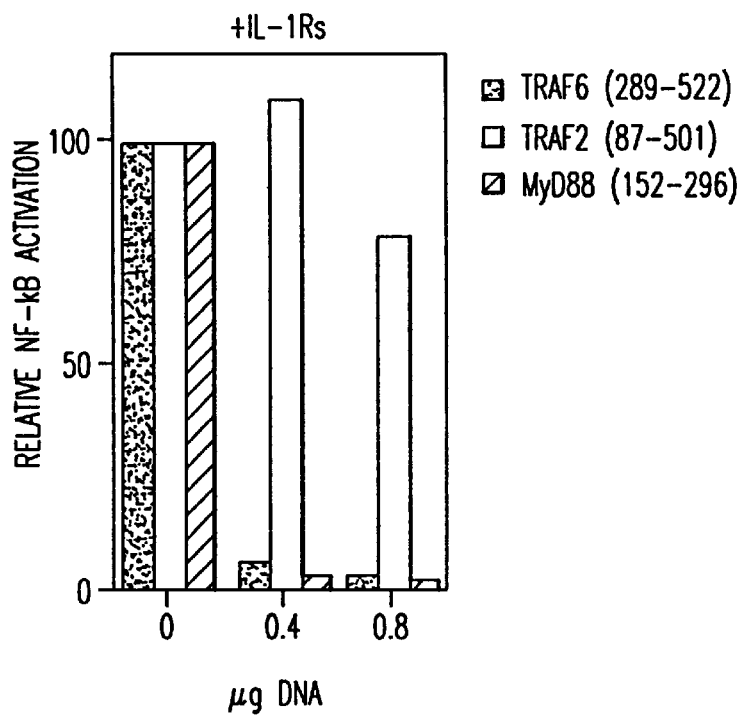
FIGS. 7A–B show that MyD88 (106–296) selectively inhibits IL-1Rs- but not TNFR2-induced NF-kB activity. TRAF6 (298–522) and the related TRAF2 (87–501) were used as controls. 0.5 μg receptors and increasing amounts of putative dominant negative expression constructs were transfected. Data are expressed as percentage of relative IL-1RS or TNFR2-induced NF-kB activity.
Figure 7B:
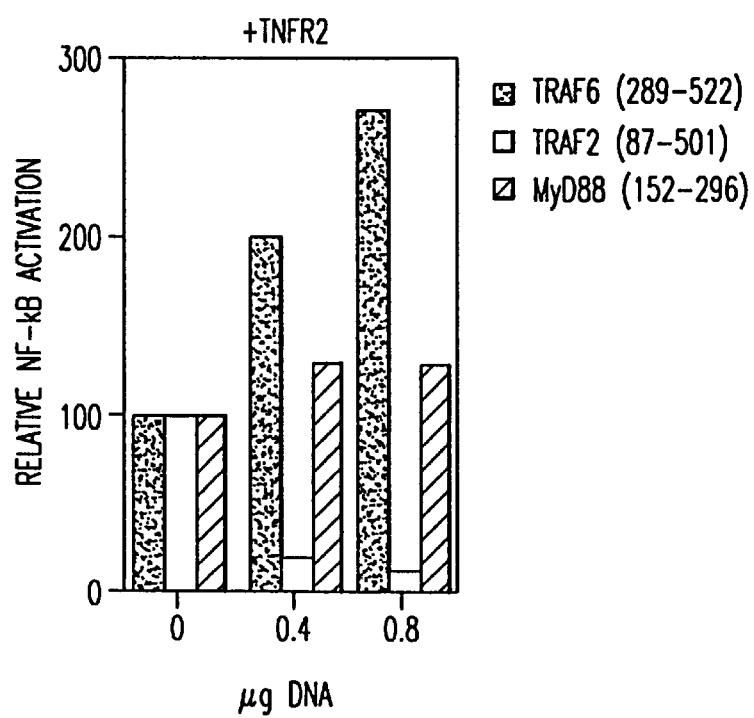
Figure 9:
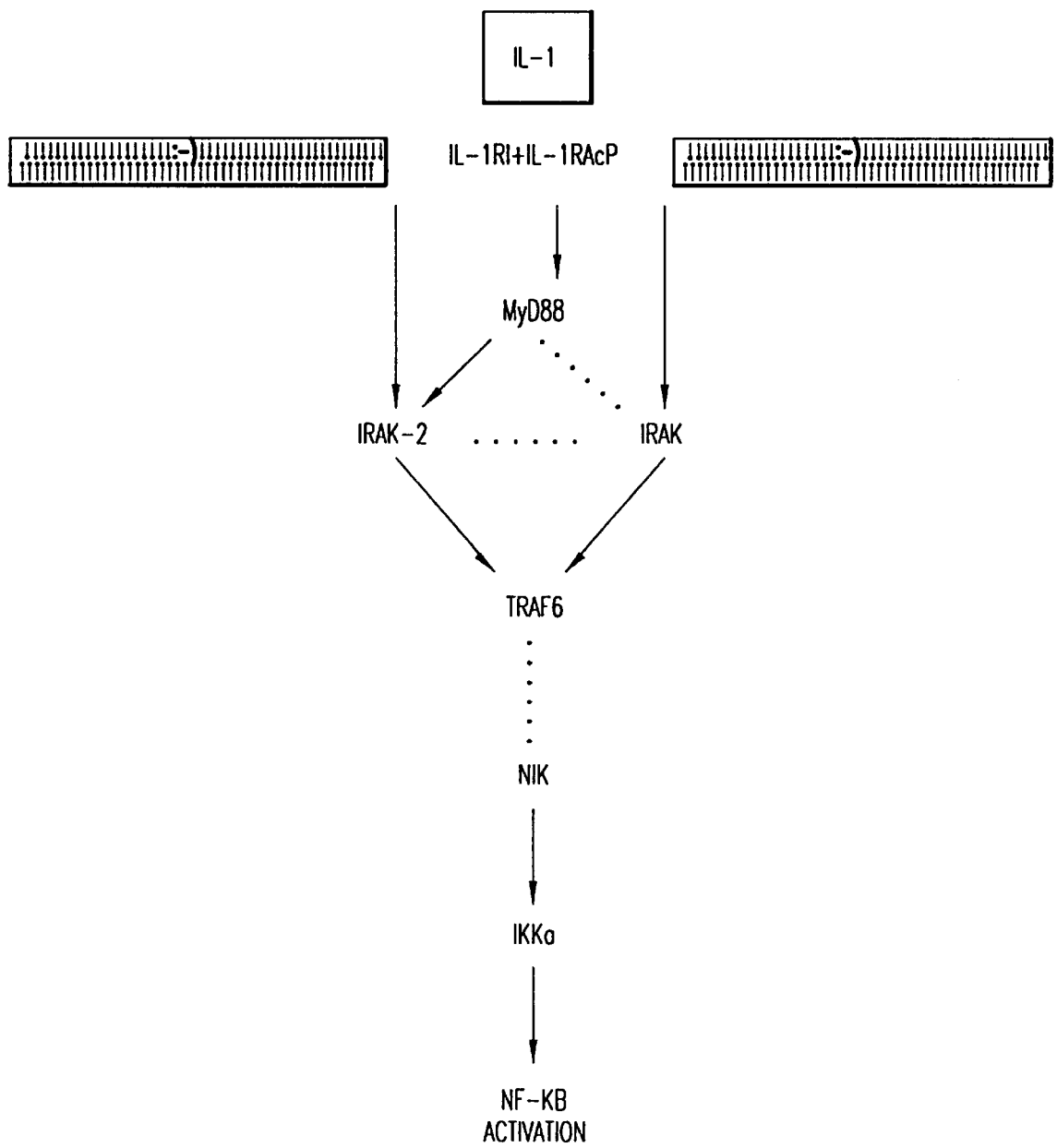
FIG. 9 is a schematic representation of the molecular order of mediators of the IL-1Rs-induced NF-kB activation.
Figure 10:
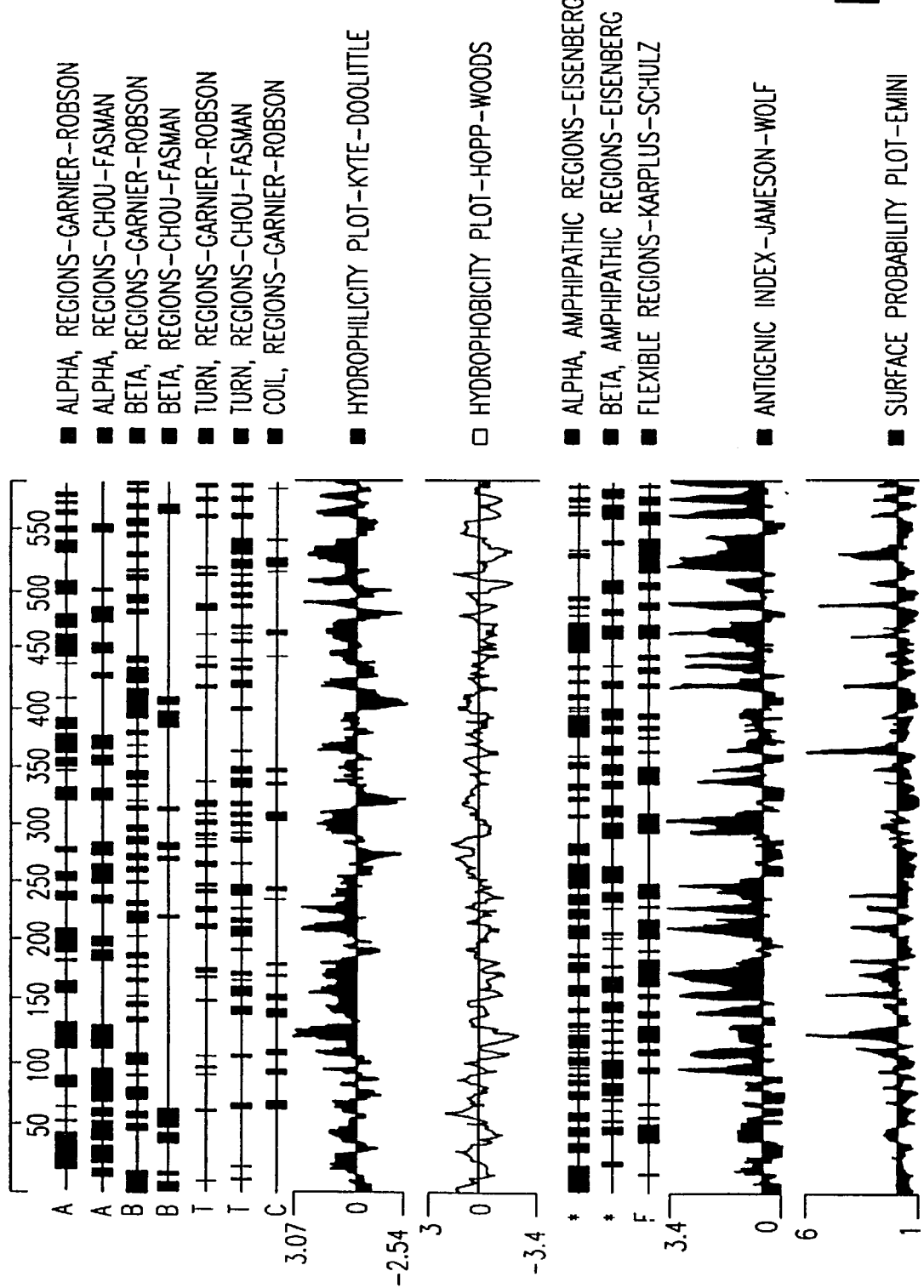
FIG. 10 shows an analysis of the IRAK-2α amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues about 96 to about 193, about 207 to about 254, about 293 to about 316, about 416 to about 472, and about 487 to about 541 in FIG. 1 (SEQ ID NO:2) correspond to the shown highly antigenic regions of the IRAK-2α protein.
Figure 11:
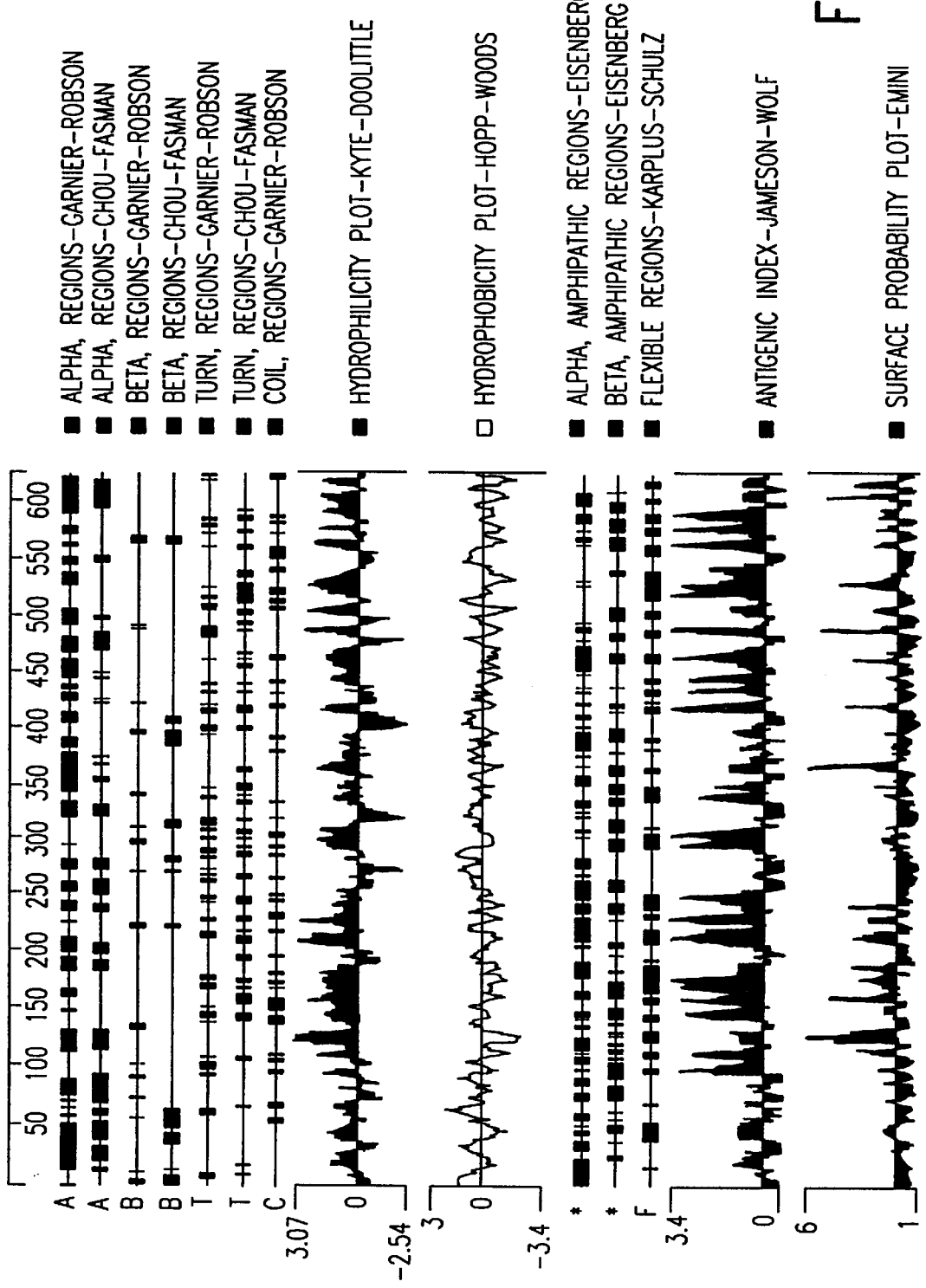
FIG. 11 shows an analysis of the IRAK-2β amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues 96 to about 193, about 207 to about 254, about 293 to about 316, about 416 to about 472, about 487 to about 541, and about 559 to about 619 in FIG. 2 (SEQ ID NO:4) correspond to the shown highly antigenic regions of the IRAK-2β protein.

Given the significant sequence homology existing between MyD88 and the IL-1RAcP, it was investigated whether the two could interact. Upon coexpression in 293T cells, MyD88 and IL-1RAcP formed an immunoprecipitable complex. IL-1RI, which shows weaker sequence similarity to MyD88, did not associate with MyD88 under these experimental conditions. Domain mapping studies revealed that the sequence homologous C-terminal region of MyD88 was sufficient for binding to the IL-1RAcP cytoplasmic domain (FIGS. 7A–7B) consistent with a hemophilic interaction.

In an effort to molecularly order the proximal components of the IL-1R signaling complex identified herein, it was tested whether the dominant negative mutant versions of MyD88 and IRAK-2 could inhibit the active forms of the others. A dominant negative version of MyD88 completely abrogated IL-1Rs-induced NF-kB activation but failed to inhibit IRAK-2-induced NF-kB activation (FIGS. 8A–8C). On the other hand, dominant negative versions of IRAK-2, significantly inhibited both IL-1Rs- and MyD88-induced NF-kB activity. These results are consistent with MyD88 acting upstream of IRAK-2 in the IL-1R signaling pathway.

Given the presence of a N-terminal "interaction domain" (DD) in both MyD88 and IRAK-2 (Feinstein, E., et al., supra; and Hofmann, K. & Tschopp, J., supra)) it was tested whether these two proteins could interact. It was found that MyD88 specifically coprecipitated with IRAK-2. Significantly a truncated version of IRAK-2 lacking the N-terminal domain (DD) [IRAK-2 (97–590)], that failed to induce NF-kB activation, also failed to associate with MyD88; similarly, the version of MyD88 (152–296) that was unable to induce NF-kB activity, was also impaired in its ability to bind IRAK-2 lending functional credence to this interaction.

Taken together these results support a model wherein MyD88 acts as an adapter/regulator in the IL-1R signaling complex by independently interacting with IL-1RAcP and IRAK-2. However, we were unable, under these experimental conditions, to assemble a multimolecular complex between MyD88, IRAK-2 and the IL-1Rs. This is consistent with the possibility that MyD88 is only transiently recruited to the IL-1R signaling complex where it subsequently regulates IRAK-2's activity.

Methods cDNA Cloning and Analysis

A partial cDNA clone was used to screen a human HUVEC cDNA library. Hybridizing clones were characterized by automated DNA sequencing. Alternatively the sequence corresponding to aa, 391 to 570 of IL-1RAcP was used to search the NCBI Gene Bank nr database. Human and murine MyD88 cDNAs were identified as having statistically significant homology to IL-1RAcP. Sequence assembly, comparison and alignment were performed using DNASTAR software.

Expression Vectors

Mammalian expression vectors encoding Flag-TRAF6, Flag-TRAF6 (289–522), Flag-TRAF2, Flag-TRAF2 (87–501), NIK (KK429–430AA), ELAM-Luciferase reporter plasmid, Flag-IL1RAcP and IRAK have been previously described ((Cao, Z., et al., Nature 383:443–6 (1996); Chinnaiyan, A., et al., Science 274:990–92 (1996); Malinin, N. L., et al., Nature 385:5:540–4(1997); and Rothe, M., et al., Science 269:1424–7 (1995)). AU1-IRAK-2 (1–96), AU1-MyD88, AU-1-MyD88 (152–296) and HA-MyD88 (1–151) were PCR amplified from a HUVEC cDNA library using custom-made oligonucleotide primers encoding the AU1 or HA epitope tag. Amplified fragments were cloned into the mammalian expression vector pCDNA3 (Invitrogen). IRAK-2-MyC and IRAK-2 (97–590)-MyC were obtained hy PCR amplification and cloned in frame into pCDNA3-MyC-His vector (Invitrogen). Flag-IL-1RI and Flag-ΔIL-1RI were similarly obtained by PCR amplification from the HUVEC cDNA library and sub cloned in frame into pCMV-1-Flag expression vector.

Transfection and Coimmunoprecipitation

Human embryonic 293 or 293T cells were transiently transfected by calcium phosphate method with the indicated plasmids. The total amount of DNA was kept constant. 24–36 hours after transfection, cells were lysed in 0.5 ml buffer (1% NP40, 150 mM NaCl, 50 mM Tris, 1 mM EDTA and protease inhibitors cocktail). Cell lysates were adjusted to 0.7 M NaCl and the indicated antibodies were added for 1 to 4 hours. Immune complexes were precipitated by the addition of protein-G-Sepharose (Sigma). After extensive washing, the Sepharose heads were boiled in sample buffer and the eluted proteins fractionated by SDS-PAGE. Subsequent protein immunoblotting was performed as described (Chinnaiyan, A., et al., Cell 81:505–12 (1995)).

NF-kB Luciferase Assay

Cells were transfected with 0.1 µg ELAM-Luciferase reporter plasmid, 0.2 µg pCMV-βGal and the indicated expression vectors; total amount of transfected DNA was kept constant by supplementation with empty vector. Relative NF-kB activity was calculated by normalizing relative luciferase activity with βGal activity as previously described (Cao, Z. et al., Nature 383:443–446 (1996)).

Example 2

Tissue Distribution of IRAK-2 mRNA Expression

Northern blot analysis is carried out to examine IRAK-2 gene expression in human tissues, using methods described by, among others, Sambrook et al., cited above. A cDNA probe containing the nucleotide sequence corresponding to the open reading frame of the IRAK-2α protein (SEQ ID NO:1) is labeled with $^{32}$p using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for IRAK-2 mRNA.

Multiple Tissue Northern (MTN) blots containing various human tissues (H) are obtained from Clontech and examined with the labeled probe using ExpressHyb™ hybridization solution (Clontech) according to manufacturer's protocol number PT1190-1. Following hybridization and washing, the blots are mounted and exposed to film at −70° C. overnight, and films developed according to standard procedures.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated antibody which specifically binds the polypeptide of SEQ ID NO:2 or SEQ ID NO:4.

2. The isolated antibody of claim 1 which specifically binds the polypeptide of amino acids 96 to 193 of SEQ ID NO:2 or SEQ ID NO:4.

3. The isolated antibody of claim 1 which specifically binds the polypeptide of amino acids 207 to 254 of SEQ ID NO:2 or SEQ ID NO:4.

4. The isolated antibody of claim 1 which specifically binds the polypeptide of amino acids 293 to 316 of SEQ ID NO:2 or SEQ ID NO:4.

5. The isolated antibody of claim 1 which specifically binds the polypeptide of amino acids 416 to 472 of SEQ ID NO:2 or SEQ ID NO:4.

6. The isolated antibody of claims which specifically binds the polypeptide of amino acids 487 to 541 of SEQ ID NO:2 or SEQ ID NO:4.

7. The isolated antibody of claim 1 which specifically binds the polypeptide of amino acids 559 to 619 of SEQ ID NO:4.

8. The isolated antibody of claim 1 which is monoclonal.

9. A composition comprising the isolated antibody of claim 1 and a pharmaceutically acceptable carrier.

10. A method of producing the isolated antibody of claim 1 comprising:
    (a) introducing an immunogen into an animal; and
    (b) recovering said antibody.

* * * * *

UNITED STATES PATENT AND TRADEMARK OFFICE
CERTIFICATE OF CORRECTION

PATENT NO. : 6,222,019 B1
DATED : April 24, 2001
INVENTOR(S) : Ni et al.

It is certified that error appears in the above-identified patent and that said Letters Patent is hereby corrected as shown below:

Column 7,
Lines 40-41, please delete "1750 nM" and insert therefor -- 750 mM --.
Line 43, please delete "20 mg/ml" and insert therefor -- 20 µg/ml --.

Column 52, claim 6,
Line 38, please delete "claims" and insert therefor -- claim 1, --.

Signed and Sealed this

Twenty-second Day of January, 2002

Attest:

Attesting Officer

JAMES E. ROGAN
Director of the United States Patent and Trademark Office